United States Patent
Garcia et al.

(10) Patent No.: US 7,846,167 B2
(45) Date of Patent: Dec. 7, 2010

(54) DRIVER ASSEMBLY AND FASTENER APPARATUS

(75) Inventors: Saddy R. Garcia, St. Augustine, FL (US); Ryan N. Luby, Atlantic Beach, FL (US); Robert T. McKee, Jacksonville, FL (US); Derek S. Lewis, Jacksonville, FL (US); Shawn D. Roman, Orange Park, FL (US); Larry Colgan, Jacksonville, FL (US)

(73) Assignee: Biomet Microfixation, LLC, Jacksonville, FL (US)

( * ) Notice: Subject to any disclaimer, the term of this patent is extended or adjusted under 35 U.S.C. 154(b) by 1056 days.

(21) Appl. No.: 11/593,447

(22) Filed: Nov. 6, 2006

(65) Prior Publication Data

US 2007/0106283 A1 May 10, 2007

Related U.S. Application Data

(60) Provisional application No. 60/734,082, filed on Nov. 7, 2005.

(51) Int. Cl.
*A61B 17/58* (2006.01)
*A61B 17/60* (2006.01)
*A61F 2/00* (2006.01)

(52) U.S. Cl. .................... 606/104; 606/99; 606/306

(58) Field of Classification Search ............ 606/104, 606/306; 433/174, 221; 81/44, 460, 186, 81/437, 461; 411/405
See application file for complete search history.

(56) References Cited

U.S. PATENT DOCUMENTS

| | | | |
|---|---|---|---|
| 1,269,971 A | 6/1918 | Smith | |
| 3,343,443 A | 9/1967 | Moore | |
| 4,096,896 A | 6/1978 | Engel | |
| 4,466,315 A | 8/1984 | Boschetto, Jr. et al. | |
| 4,480,514 A | 11/1984 | Ponziani | |
| 4,923,471 A | 5/1990 | Morgan | |
| D327,824 S | 7/1992 | Bianco, Sr. | |
| 5,624,216 A * | 4/1997 | Detable et al. ........... | 411/5 |
| 5,690,639 A | 11/1997 | Lederer et al. | |
| 5,735,854 A | 4/1998 | Caron et al. | |
| 5,928,236 A | 7/1999 | Augagneur et al. | |
| 5,971,987 A * | 10/1999 | Huxel et al. ............. | 606/916 |
| 6,077,267 A * | 6/2000 | Huene ................... | 606/916 |
| 6,206,696 B1 | 3/2001 | Day | |
| 6,217,332 B1 | 4/2001 | Kumar | |
| 6,247,933 B1 | 6/2001 | Wagner et al. | |
| 6,440,136 B1 | 8/2002 | Gambale et al. | |
| 6,477,923 B2 | 11/2002 | Amis | |

(Continued)

*Primary Examiner*—Thomas C Barrett
*Assistant Examiner*—Andrew Yang
(74) *Attorney, Agent, or Firm*—Harness, Dickey

(57) ABSTRACT

A driver assembly may include a fastener and a driver. The fastener may have a head with upper and lower surfaces. An engagement portion may be located in the upper surface proximate a perimeter portion thereof. A shank may extend from the lower surface of the head and a breakaway portion may extend from the upper surface of the head. The driver may include a shaft having a body with a first end having a fastener-engaging portion. The fastener-engaging portion may have an outer driving geometry engaged with the engagement portion of the fastener when in an engaged position. The first end may further include an opening therein. The opening may receive at least a portion of the breakaway portion when in the engaged position.

11 Claims, 25 Drawing Sheets

U.S. PATENT DOCUMENTS

| | | |
|---|---|---|
| 6,561,805 B2 | 5/2003 | Kumar |
| 6,589,244 B1 | 7/2003 | Sevrain et al. |
| 6,811,552 B2 | 11/2004 | Weil, Sr. et al. |
| 6,875,215 B2 | 4/2005 | Taras et al. |
| 6,884,244 B1 | 4/2005 | Jackson |
| 7,022,129 B2 | 4/2006 | Overaker et al. |
| 2003/0158556 A1* | 8/2003 | Taras et al. .................... 606/73 |
| 2004/0018471 A1* | 1/2004 | Giorno ....................... 433/174 |
| 2005/0010300 A1 | 1/2005 | Disilvestro et al. |
| 2005/0165402 A1 | 7/2005 | Taras |
| 2005/0177243 A1 | 8/2005 | Lepow et al. |

* cited by examiner

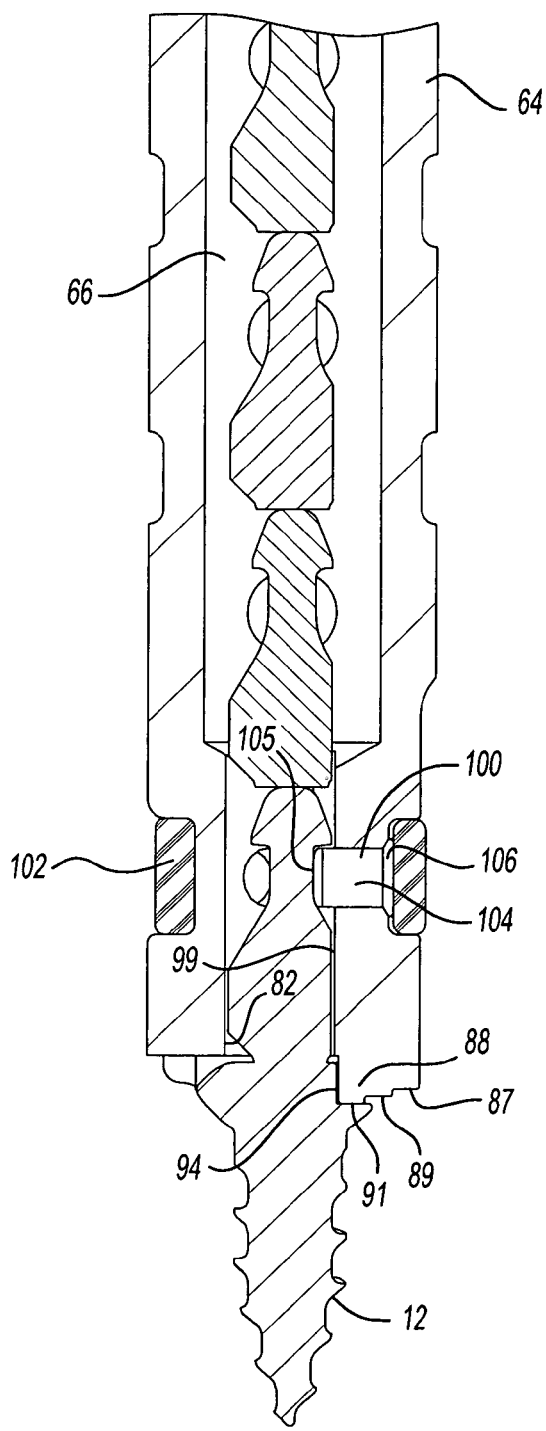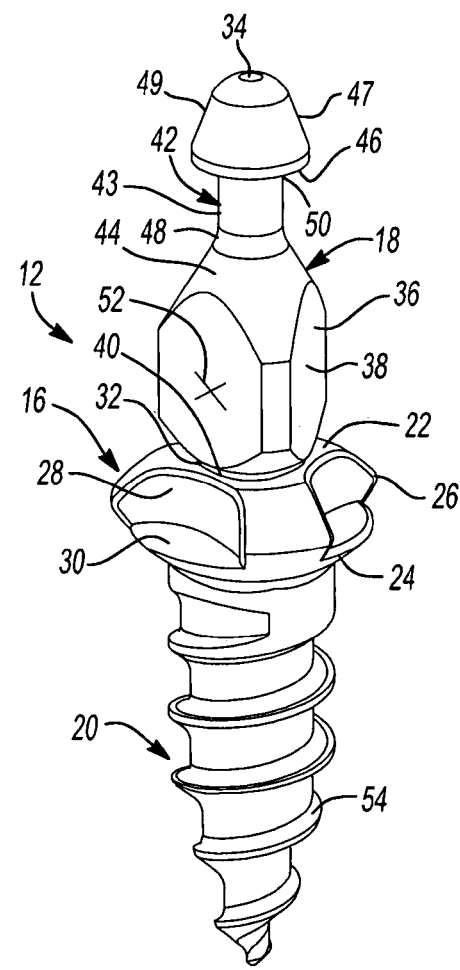
Fig-3
Fig-4

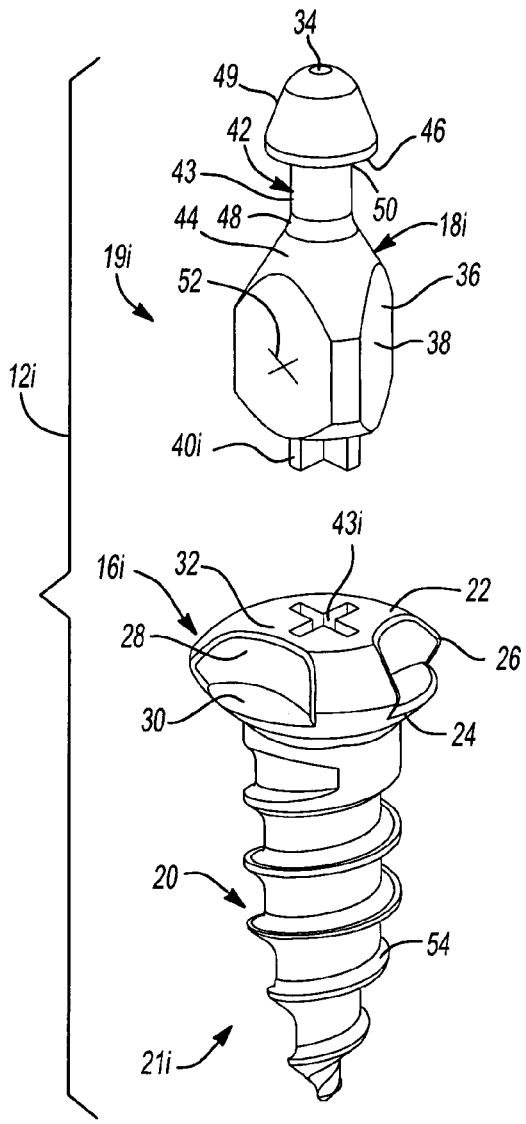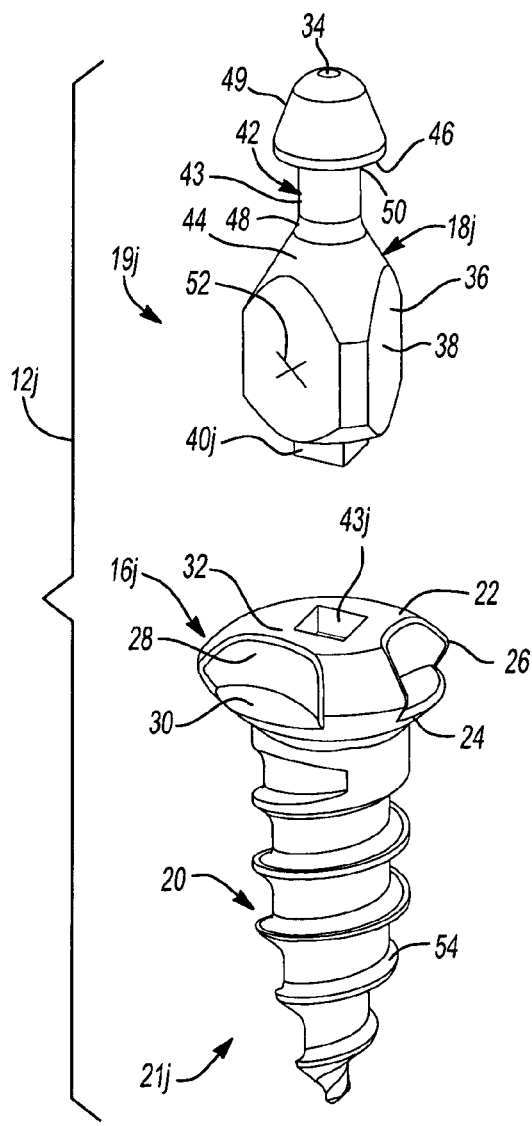
Fig-13
Fig-14

DRIVER ASSEMBLY AND FASTENER APPARATUS

CROSS-REFERENCE TO RELATED APPLICATIONS

This application claims the benefit of U.S. Provisional Application No. 60/734,082, filed on Nov. 7, 2005, the disclosure of which is incorporated herein by reference in its entirety.

FIELD

The present teachings relate to a driver assembly, and more specifically to a medical driver assembly.

BACKGROUND

Medical drivers typically have unique driving arrangements for different fastener sizes. Many drivers and fasteners are also difficult to manufacture due to tight tolerances required for interference-fit engagements. Current fasteners may also be difficult to track once coupled to a structure.

SUMMARY

A driver assembly may include a fastener and a driver. The fastener may have a head with upper and lower surfaces. An engagement portion may be located in the upper surface proximate a perimeter portion thereof. A shank may extend from the lower surface of the head and a breakaway portion may extend from the upper surface of the head. The driver may include a shaft having a body with a first end having a fastener-engaging portion. The fastener-engaging portion may have an outer driving geometry engaged with the engagement portion of the fastener when in an engaged position. The first end may further include an opening therein. The opening may receive at least a portion of the breakaway portion when in the engaged position.

Further areas of applicability of the present teachings will become apparent from the detailed description provided hereinafter. It should be understood that the detailed description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein:

FIG. 3 is a fragmentary sectional view of the driver assembly shown in FIG. 1;
FIG. 4 is a perspective view of the fastener shown in FIG. 1;
FIG. 13 is a perspective exploded view of an additional fastener;
FIG. 14 is a perspective exploded view of an additional fastener.

DETAILED DESCRIPTION

Figure 1:
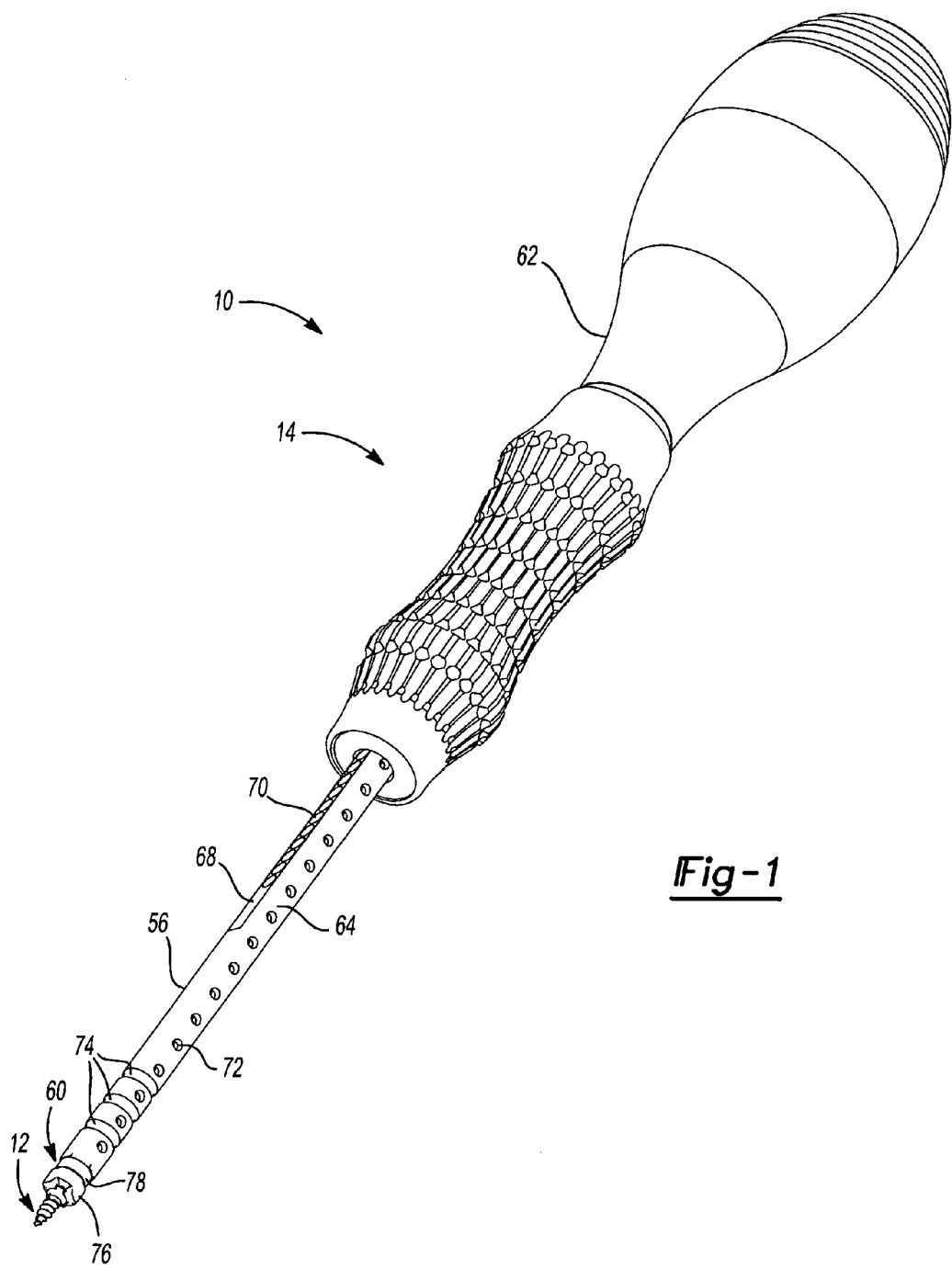
FIG. 1 is a perspective view of a first driver assembly.

The following description is merely exemplary in nature and is not intended to limit the present disclosure, application, or uses. It should be understood that throughout the drawings, corresponding reference numerals indicate like or corresponding parts and features.

Figure 2:
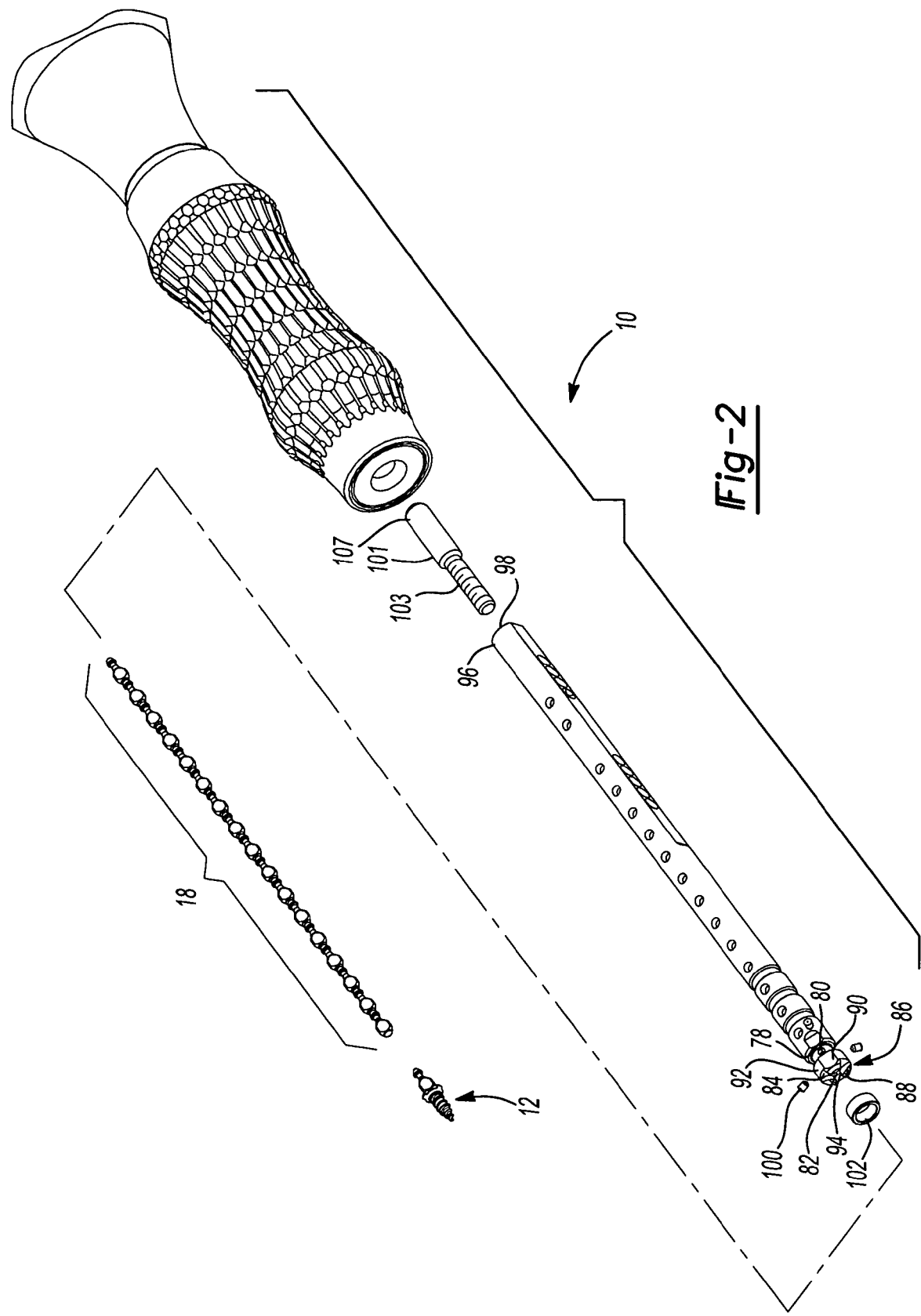
FIG. 2 is an exploded view of the driver assembly of FIG. 1.

FIGS. 1-3 generally show a driver assembly 10, which may include a fastener 12 and a driver 14. A variety of fasteners are shown in FIGS. 4-21. Numerous features may be common between the fasteners shown in FIGS. 4-21. Therefore, it is understood that the description of fastener 12 shown in FIG. 4 applies equally to FIGS. 5-21 where common reference numerals are used.

Figure 16:
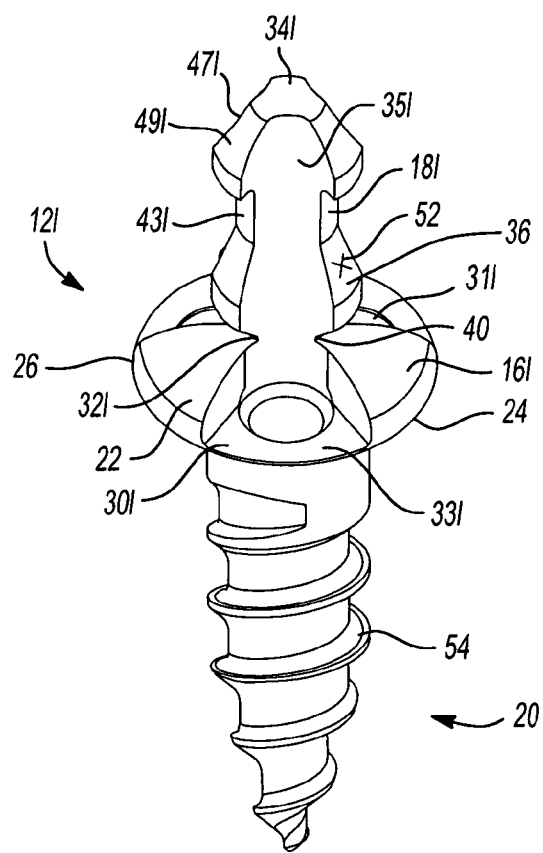
FIG. 16 is a perspective view of an additional fastener.
Figure 17:
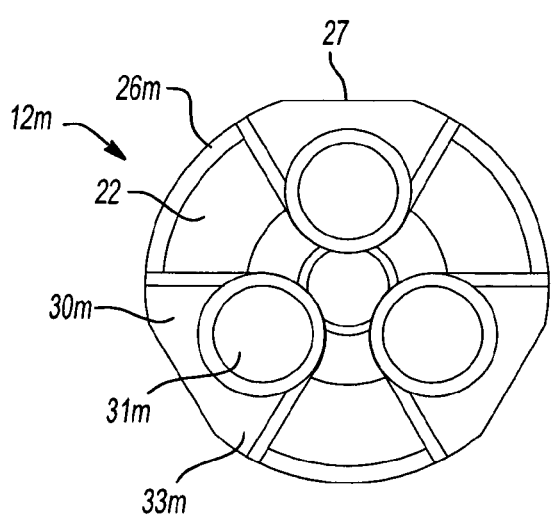
FIG. 17 is a top plan view of a head portion of an additional fastener.
Figure 18:
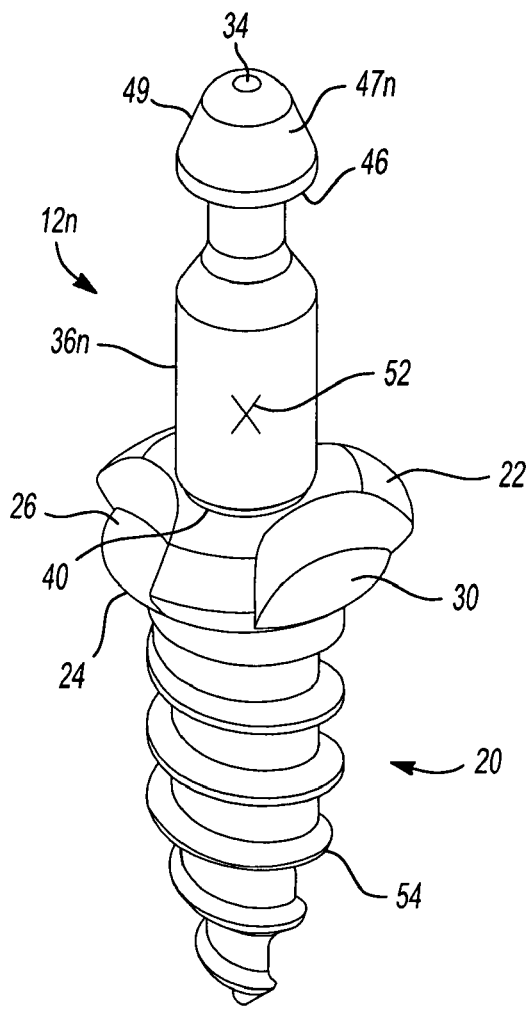
FIG. 18 is a perspective view of an additional fastener.
Figure 19:
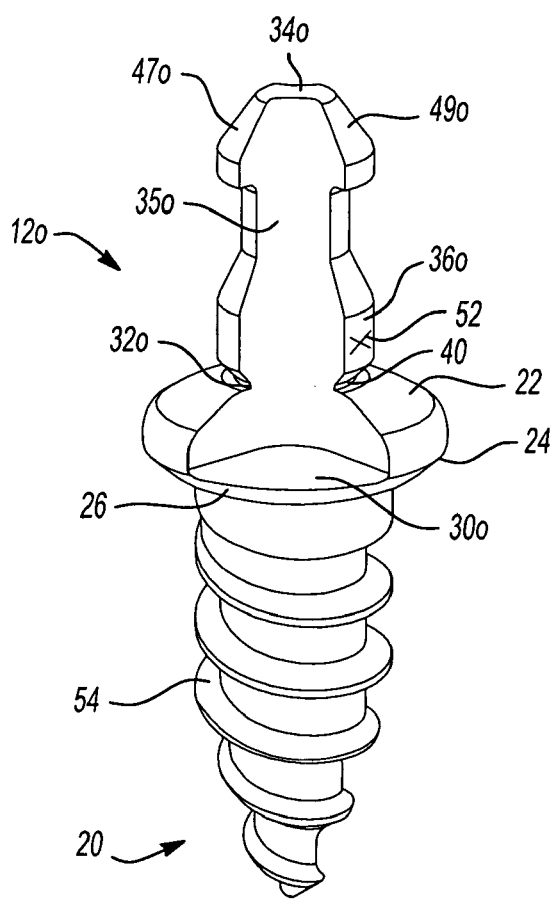
FIG. 19 is a perspective view of an additional fastener.

With reference to FIG. 4, fastener 12 may include a head 16, a post 18 and a shank 20. The head 16 may include an upper surface 22, a lower surface 24 and a perimeter portion 26 disposed between the upper and lower surfaces 22, 24. Perimeter portion 26 may be generally circular (as seen in FIGS. 4-16 and 18-21) or, as seen in FIG. 17, perimeter portion 26m may include alignment features such as flats 27 for aligning fastener 12m within a cartridge (not shown). The upper surface 22 may include a driving geometry 28 near the perimeter portion 26. The driving geometry 28 may be in the form of arcuate recesses 30. While three (3) arcuate recesses 30 are shown in FIG. 4, it should be understood that more or less may be used. For example, as seen in FIG. 19, a fastener 12o may include two recesses 30o. Recesses 30 do not need to be arcuate in form and may include a variety of shapes. The driving geometry, including the number of recesses 30, may be common for a variety of fasteners of different sizes and even different materials.

Figure 5:
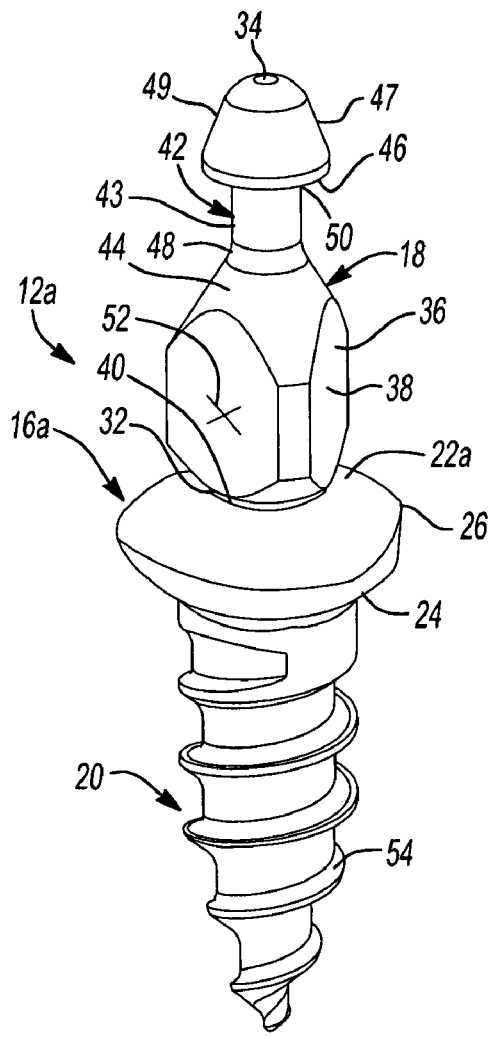
FIG. 5 is a perspective view of an additional fastener.

As seen in FIG. 5, fastener 12a may include an upper surface 22a of head 16a being generally continuous and having no recesses at all. Alternatively, as seen in FIGS. 16 and 17, fasteners 12l, 12m may include recessed portions 30l, 30m generally similar to recesses 30 seen in FIGS. 4 and 6-15, 18, 20 and 21 with additional driving features such as recesses 31l, 31m. Recesses 31l, 31m may extend axially into an upper surface 33l, 33m of recess 30l, 30m and may be generally circular. Recesses 31l, 31m may provide an additional location for engagement with a driver, as discussed below.

Figure 6:
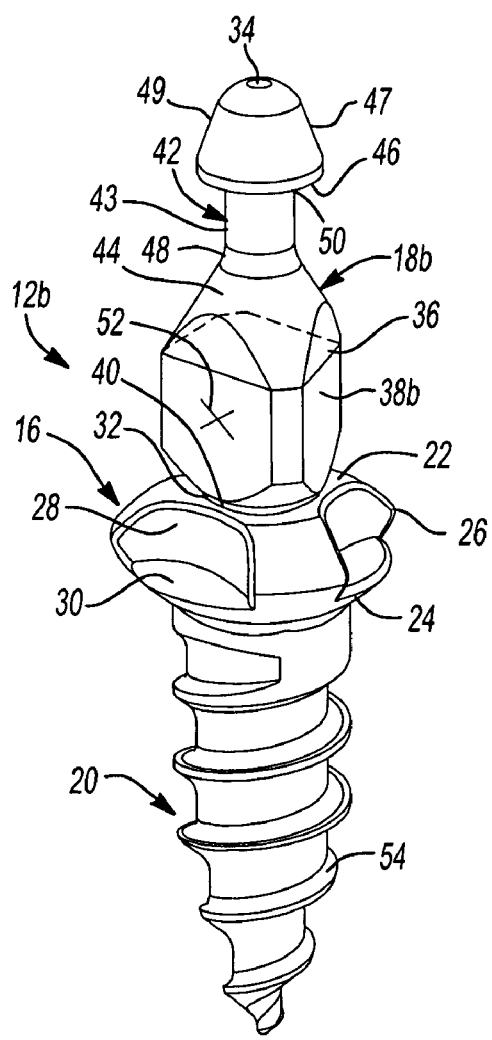
FIG. 6 is a perspective view of an additional fastener.
Figure 7:
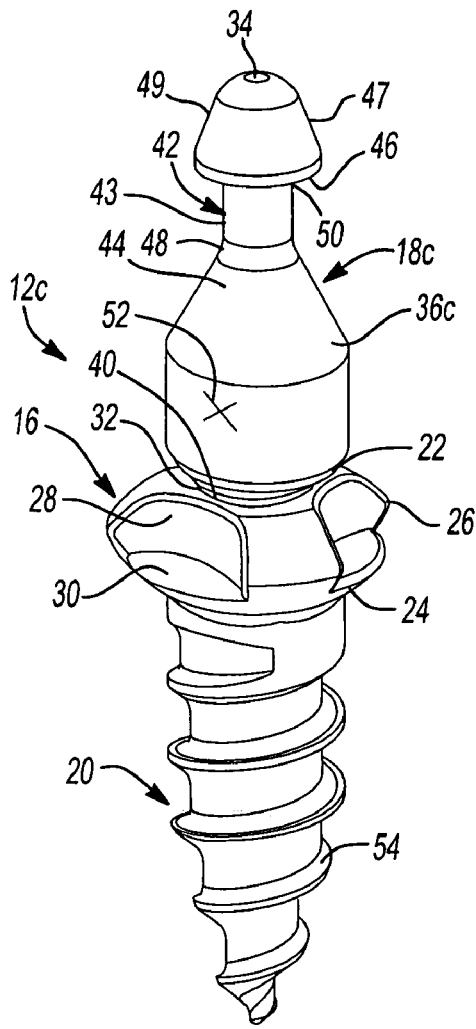
FIG. 7 is a perspective view of an additional fastener.
Figure 8:
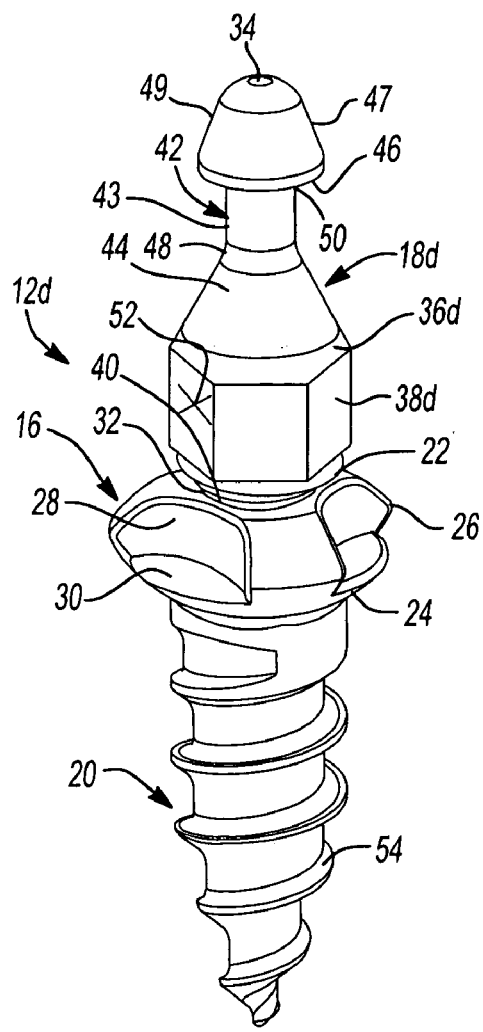
FIG. 8 is a perspective view of an additional fastener.

The post 18 may include first and second ends 32, 34. A main body portion 36 may be disposed between the first and second ends 32, 34. The main body portion 36 may be located proximate the upper surface 22 of head 16. A plurality of flats 38 may be formed on the main body portion 36, creating a generally triangular cross-section. Flats 38 may provide an additional driving structure for the fastener 12, as well as an alignment feature for recesses 30 and driver 14, as discussed below. In the configuration of FIG. 5, where there are no recesses, flats 38 may provide the only driving structure. A variety of other cross-sections may also be used, such as square (as seen in FIG. 6), round (having no flats, as seen in FIGS. 7 and 18) and hex (as seen in FIG. 8).

The number of recesses 30 may be the same as the number of flats 38, 38b. As seen in FIGS. 16 and 19, recessed portions 35l, 35o may be used in place of flats 38. Recessed portions 35l, 35o may extend from first ends 32l, 32o of posts 18l, 18o near recesses 30l, 30o to second ends 34l, 34o and may provide additional driving structure for fasteners 12l, 12o, as well as alignment features for recesses 30l, 30o and a driver, as discussed below.

Figure 20:
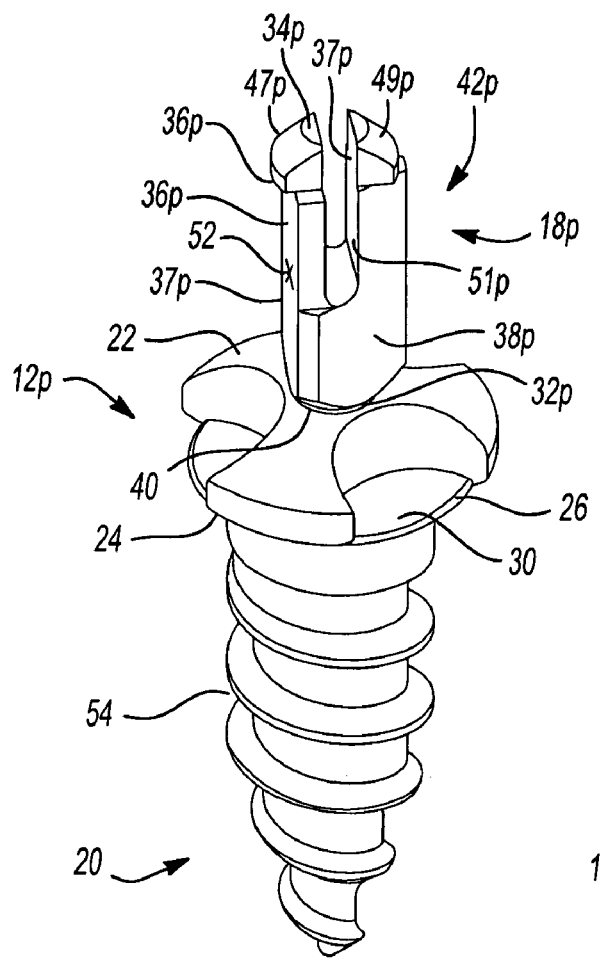
FIG. 20 is a perspective view of an additional fastener.
Figure 21:
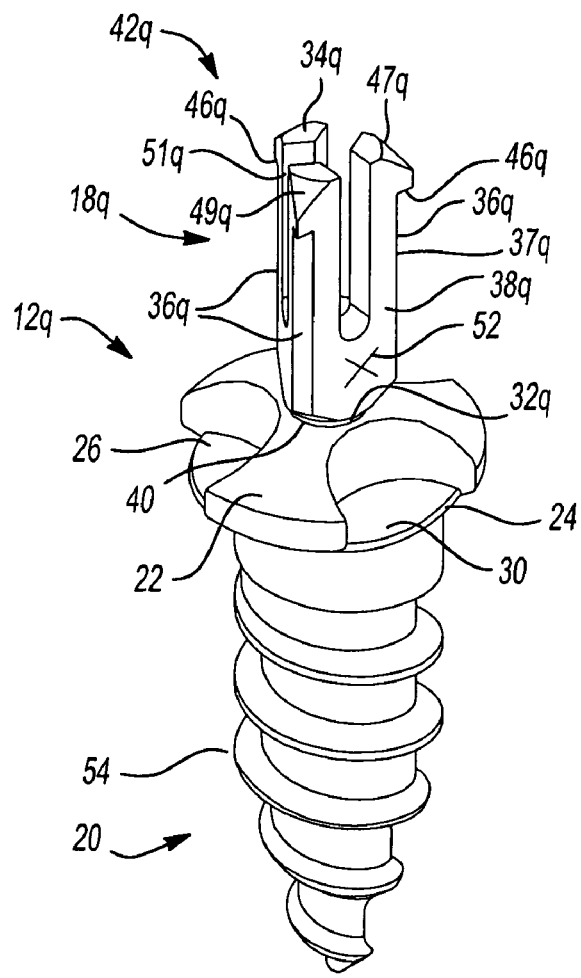
FIG. 21 is a perspective view of an additional fastener.

With additional reference to FIGS. 20 and 21, alternative posts 18p, 18q may be used in place of post 18. Posts 18p, 18q may include first and second ends 32p, 32q and 34p, 34q. Post 18p may include two arms 37p extending generally parallel to one another and post 18q may include three arms 37q extending generally parallel to one another. Posts 18p, 18q may have flats 38p, 38q formed thereon generally similar to flats 38. Posts 18p, 18q may include recesses 51p, 51q therebetween to facilitate engagement with a driver, as discussed below.

Figure 9:
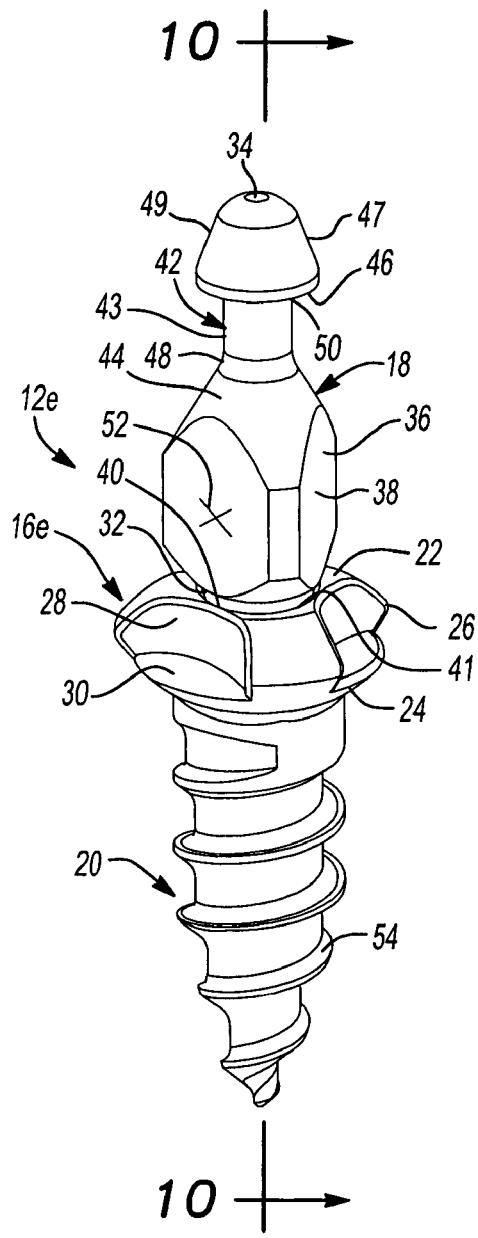
FIG. 9 is a perspective view of an additional fastener.
Figure 10:
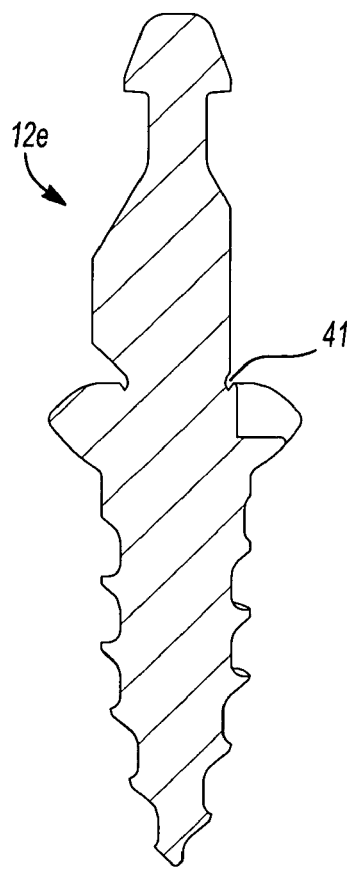
FIG. 10 is a section view of the fastener shown in FIG. 9.

The post 18 may generally form a breakaway portion of the fastener 12. A breakaway connection 40 may couple post 18 to head 16 at first end 32, allowing post 18 to be selectively separated from fastener 12. A recessed portion 41 may generally surround breakaway connection 40, as shown in FIGS. 9 and 10. Recessed portion 41 may provide protection from any burrs, or any other material deformity, that may be formed near breakaway portion 40 when post 18 is separated from fastener head 16e. Recessed portion 41 may provide this burr protection by allowing the breakaway connection 40 to be located below an uppermost surface of fastener head 16e.

Figure 11:
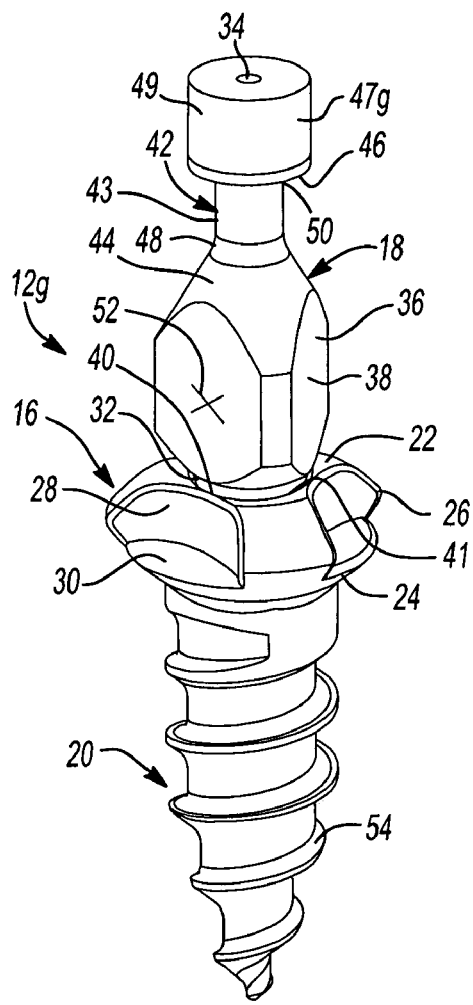
FIG. 11 is a perspective view of an additional fastener.

A retaining feature 42 may be located between main body portion 36 and second end 34. The retaining feature 42 may include a generally recessed portion 43 having walls 44, 46 extending generally radially outwardly and defining ends 48, 50 of the retaining feature 42. Wall 44 may have a generally sloped surface, assisting with engagement of post 18 with driver 14, as discussed below. An end portion 47 may include a downwardly sloped surface 49 connecting wall 46 and second end 34 (see FIG. 4). Alternatively, surface 49 may be generally straight. More specifically, end portion 47g may be cylindrical as seen in FIG. 11.

Figure 12:
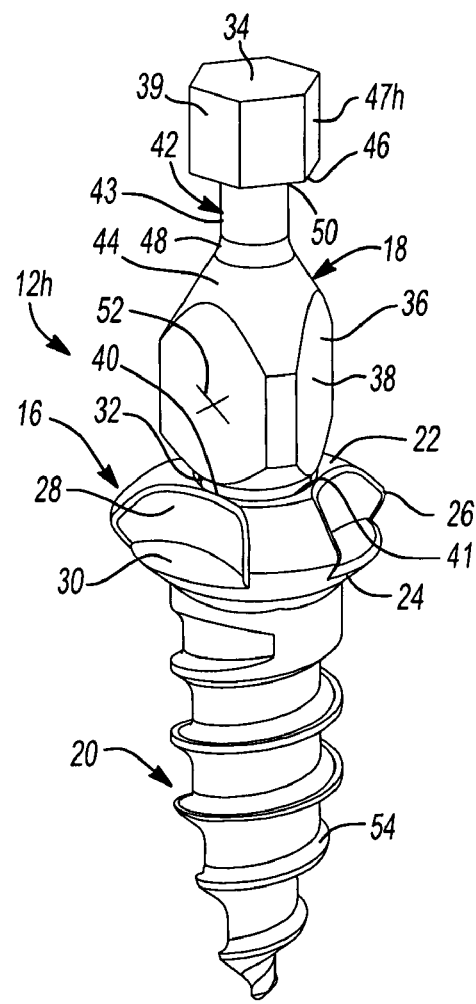
FIG. 12 is a perspective view of an additional fastener.

As seen in FIG. 12, fastener 12h may include an alternate end portion 47h having flats 39 generally corresponding to flats 38 on main body portion 36, providing an additional engagement structure. Alternatively, end portions 47l, 47o may have recessed portions 35l, 35o extending into sloped surfaces 49l, 49o, as discussed above and shown in FIGS. 16 and 19. As seen in FIGS. 4-15, end portion 47 may have a diameter that is smaller than the diameter of main body portion 36. Alternatively, as shown in FIGS. 12 and 18, end portions 47h, 47n may have a diameter generally equal to the diameter of main body portion 36, 36n. The size of the post 18 may be common for a variety of different fastener sizes.

As seen in FIGS. 20 and 21, sloped surfaces 49p, 49q of end portions 47p, 47q may alternatively include slots 51p, 51q extending therethrough, as discussed above. End portions 47p, 47q may include walls 46p, 46q extending radially outwardly relative to a body portion 36p, 36q thereof forming retaining features 42p, 42q for engagement with a driver, as discussed below.

The post 18 may further include an identifying feature 52, which may be located on a flat 38 or any other appropriate location on the post 18. The identifying feature 52 may include a visible marking made in a variety of ways including inscribing and laser etching. The identifying feature 52 may include the part number and/or the lot number of the fastener used. The identifying feature 52 may also include Radio Frequency Identification, allowing digital recording of the part number and lot number of the fastener 12 used.

The shank 20 may generally extend from the lower portion 24 of head 16. Shank 20 may include a threading 54 thereon and may be in a variety of forms such as self-drilling and self-tapping.

Figure 15:
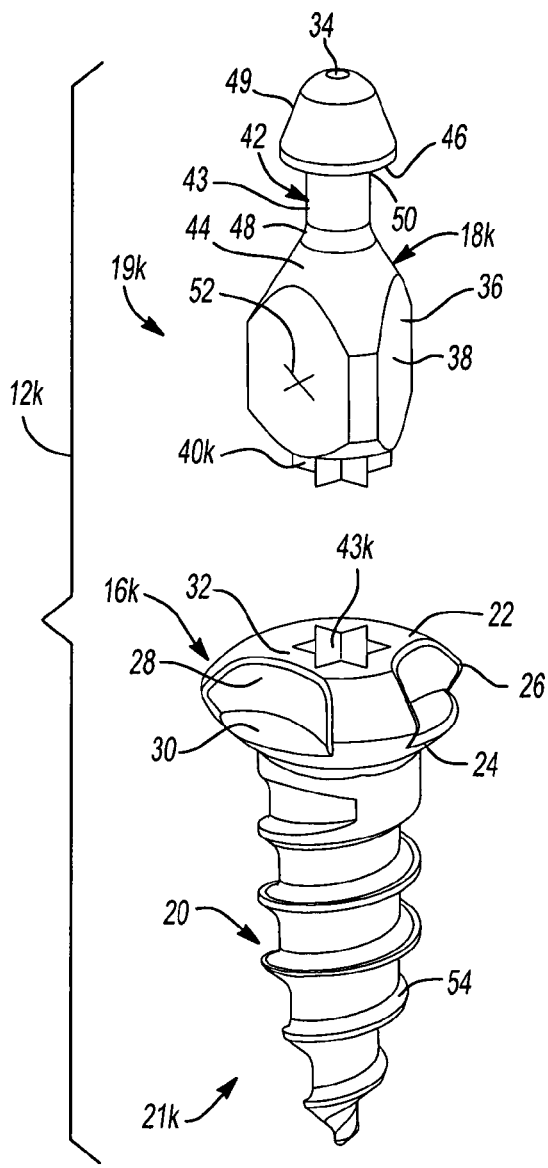
FIG. 15 is a perspective exploded view of an additional fastener.

The head 16, post 18 and shank 20 may be formed as a single piece from a desired material, or from multiple pieces, as seen in FIGS. 13-15, where the post 18i, 18j, 18k may be formed from a first piece 19i, 19j, 19k and the head 16i, 16j, 16k and shank 20 may be formed from a second piece 21i, 21j, 21k. It should be understood that all of the geometrical variations mentioned regarding the single piece fastener 12-12h may apply to a multiple-piece fastener as well. The first piece 19i, 19j, 19k and second piece 21i, 21j, 21k may be press-fit and held together through an interference fit. A variety of geometries may be used including, but are not limited to, a cross-drive, a square-drive, and a Torx® brand (available from Textron, Inc. of Providence, R.I., U.S.A.).

The breakaway portion 40i, 40j, 40k of fasteners 12i, 12j, 12k may generally extend from first end 32 of post 18i, 18j, 18k. The breakaway portion 40i, 40j, 40k may include a cross-section of any suitable geometry including those mentioned above (cross-drive, square-drive, Torx® brand, etc.). Fastener head 16i, 16j, 16k may include a generally centrally located recess 43i, 43j, 43k that has a cross-section generally similar to the cross-section of breakaway portion 40. There may, however, be slight variations between recess 43i, 43j,

43k and breakaway portion 40i, 40j, 40k. The remainder of breakaway portion 40i, 40j, 40k may still form an interference for engagement with recess 43i, 43j 43k. Breaking off posts 18i, 18j, 18k may result in the posts 18i, 18j, 18k being removed with a slight deformation to the receiving recess 43i, 43j, 43k in fastener head 16i, 16j, 16k.

The driver 14 may include a shaft 56, a retaining member 60 and a handle 62. The shaft 56 may be adjustably and removably coupled to the handle 62. Retaining member 60 may be coupled to shaft 56. The shaft 56 may include a generally cylindrical body portion 64 and a generally hollow portion 66. Shaft 56 may be formed from a generally rigid material, such as stainless steel, and may be reusable once it has been sterilized. Alternatively, shaft 56 may be a disposable unit.

The body portion 64 may include a series of flats 68. The flats 68 may include a series of dimples 70 for engagement with handle 62, discussed in more detail below. The body portion 64 may further include a series of apertures 72 extending radially through generally hollow portion 66. A series of annular grooves 74 may also be located in body portion 64. The annular grooves 74 may be painted different colors or have other identifying features indicating the type of fasteners suitable for the driver 14.

A first end 76 of body portion 64 may include an annular groove 78. The annular groove 78 may include a series of apertures 80 extending radially therethrough. The groove 78 and apertures 80 may be used in combination with the retaining member 60, discussed in more detail below. The first end 76 may also include an opening 82 in communication with the generally hollow portion 66. The opening 82 may be generally radially centered on end surface 84 of first end 76. A fastener-engaging portion 86 may extend from the first end 76 generally around opening 82.

Figure 22:
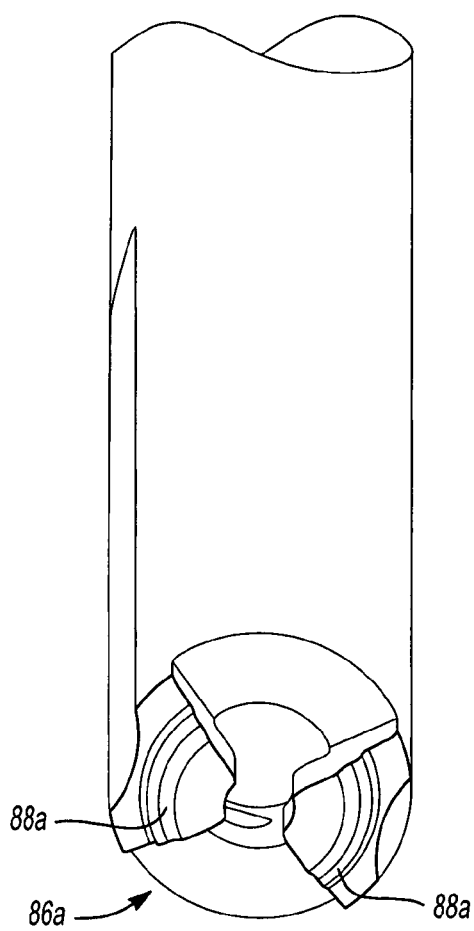
FIG. 22 is a fragmentary perspective view of an additional shaft for a driver.

The fastener-engaging portion 86 may include a series of protrusions 88. The protrusions 88 may have outer portions 90 generally aligned with an outer surface 92 of the first end 76. Outer portions 90 may be in the form of grooves or flats and may extend along a length of shaft 56, providing an alignment feature between driver 14 and a fastener cartridge (not shown). An inner portion 94 of each protrusion 88 may have a generally arcuate shape. The arcuate shape of protrusions 88 may be generally similar to arcuate recesses 30 in fastener 12. Alternatively, protrusions 88 may be a variety of other shapes, having different inner and outer portions similar to another specific fastener driving geometry. Further yet, different quantities of protrusions may be used. For example, as seen in FIG. 22, a fastener engaging portion 86a may include two protrusions 88a for engagement with a fastener such as fastener 12o (seen in FIG. 19) having two recesses 30o. Alternatively, protrusions 88 may not be specific to any specific fastener driving geometry. Shaft 56 may be engaged with a fastener such as fastener 12a shown in FIG. 5 having no recesses, discussed in greater detail below.

Protrusions 88 may additionally include a series of stepped portions 87, 89, 91. Stepped portion 87 may be the base of protrusion 88 and may have a first diameter. Stepped portion 89 may extend axially from stepped portion 87 and may have a second diameter less than the first diameter. Stepped portion 91 may extend axially from stepped portion 89 and may have a third diameter less than the second diameter.

The generally hollow portion 66 may be located within and generally extend the entire length of body portion 64. As previously mentioned, the generally hollow portion 66 may extend through first end 76 at opening 82. The generally hollow portion 66 may also extend through a second end 96 at a second opening 98. A plug 101 may be coupled to second end 96 through a threaded engagement between a first portion 103 of plug 101 and second opening 98. A second portion 107 of plug 101 may extend beyond second end 96 to accommodate removal of plug 101. The generally hollow portion 66 may have a generally triangular cross-section, similar to the cross-section of main body portion 36 of post 18. This cross-section may include a plurality of flats 99 generally similar to flats 38 on fastener post 18. Alternatively, this cross-section may be a variety of other shapes conforming to a fastener post, such as circular, hexagonal and square, as mentioned above. In yet another variation, the generally hollow portion 66 may have a cross-section that does not conform to a cross-section of a fastener post. For example, generally hollow portion 66 may have a circular cross-section sized to accept post 18 with a triangular cross-section. Further, generally hollow portion 66 may have a combination of different cross-sectional shapes. A sleeve (not shown) may be contained within the generally hollow portion 66 for containing broken-off portions of posts 18.

The retaining member 60 may include a series of pins 100 and an outer ring member 102. The pins 100 may be generally cylindrical members having first and second body portions 104, 106. The first body portion 104 may have a diameter generally equal to the diameter of aperture 80. The first body portion 104 may further include a first end 105 having a generally rounded surface. The second body portion 106 may have a diameter greater than the diameter of apertures 80. The first body portion 104 may extend through apertures 80, positioning first end 105 within generally hollow portion 66. Second body portion 106 may generally abut groove 78, preventing pins 100 from completely passing through apertures 80. The outer ring member 102 may retain pins 100 within apertures 80.

The outer ring member 102 may be in the form of a generally annular sleeve having a width generally equal to the width of groove 78. The outer ring member 102 may generally surround groove 78 and urge second body portion 106 of pins 100 against groove 78. The outer ring member 102 may be formed from an elastic material, which allows pins 100 to be displaced radially outwardly when acted upon by a sufficient force from a member within generally hollow portion 66.

Figure 23:
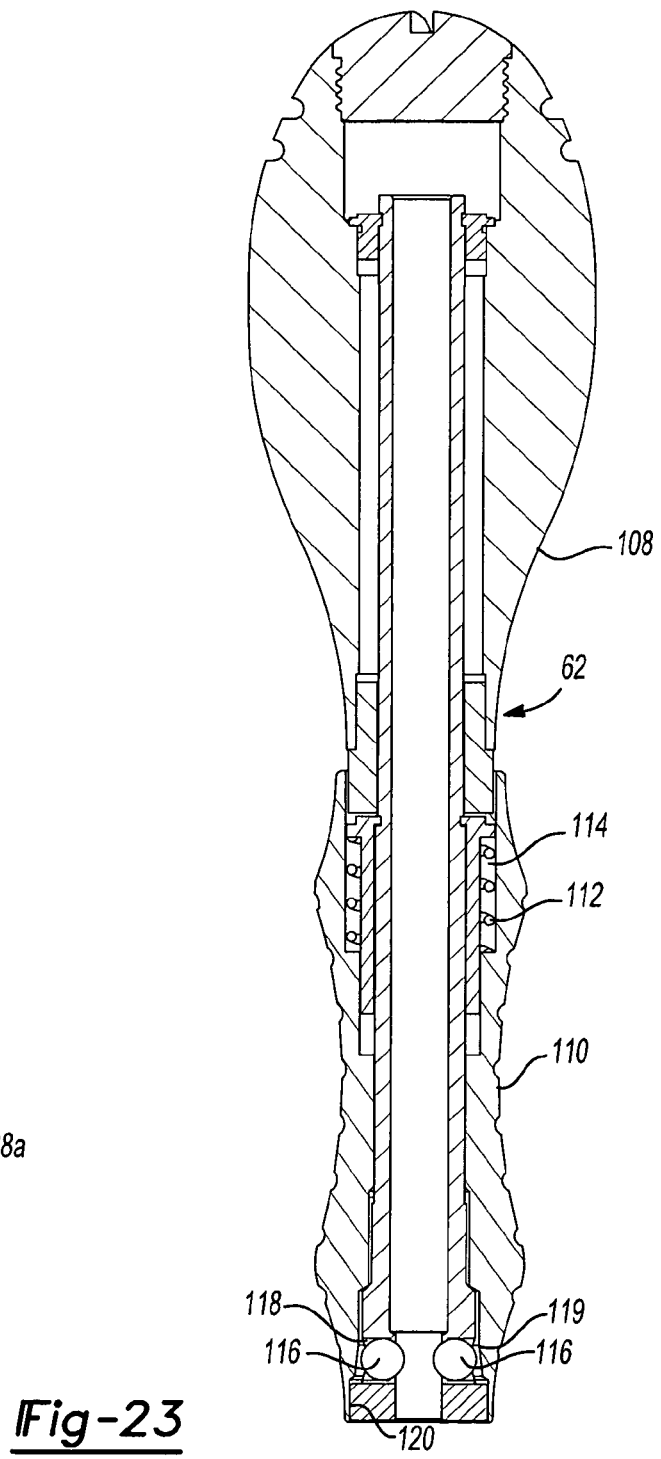
FIG. 23 is a sectional view of the driver handle shown in FIG. 1.

With additional reference to FIG. 23, the second end 96 of shaft 56 may extend into handle 62. The handle 62 may include a base portion 108 and a gripping portion 110. The gripping portion 110 may be slidably coupled to base portion 108. A spring 112 may be disposed in an annular recess 114 between the base and gripping portions 108, 110. The spring 112 may provide a force generally biasing gripping portion 110 in a direction toward shaft 56. A series of balls 116 may be located in recesses 118 and provide selective engagement between handle 62 and shaft 56. When engaged, balls 116 are urged inwardly by an engagement surface 119 of gripping portion 110 against a dimple 70, preventing axial travel of shaft 56. When gripping portion 110 is axially displaced, balls 116 may be disengaged. The balls 116 may then be free to move radially outwardly due to the larger diameter disengagement surface 120 being translated over balls 116. This allows shaft 56 to be removed or axially displaced further into handle 62.

Figure 24:
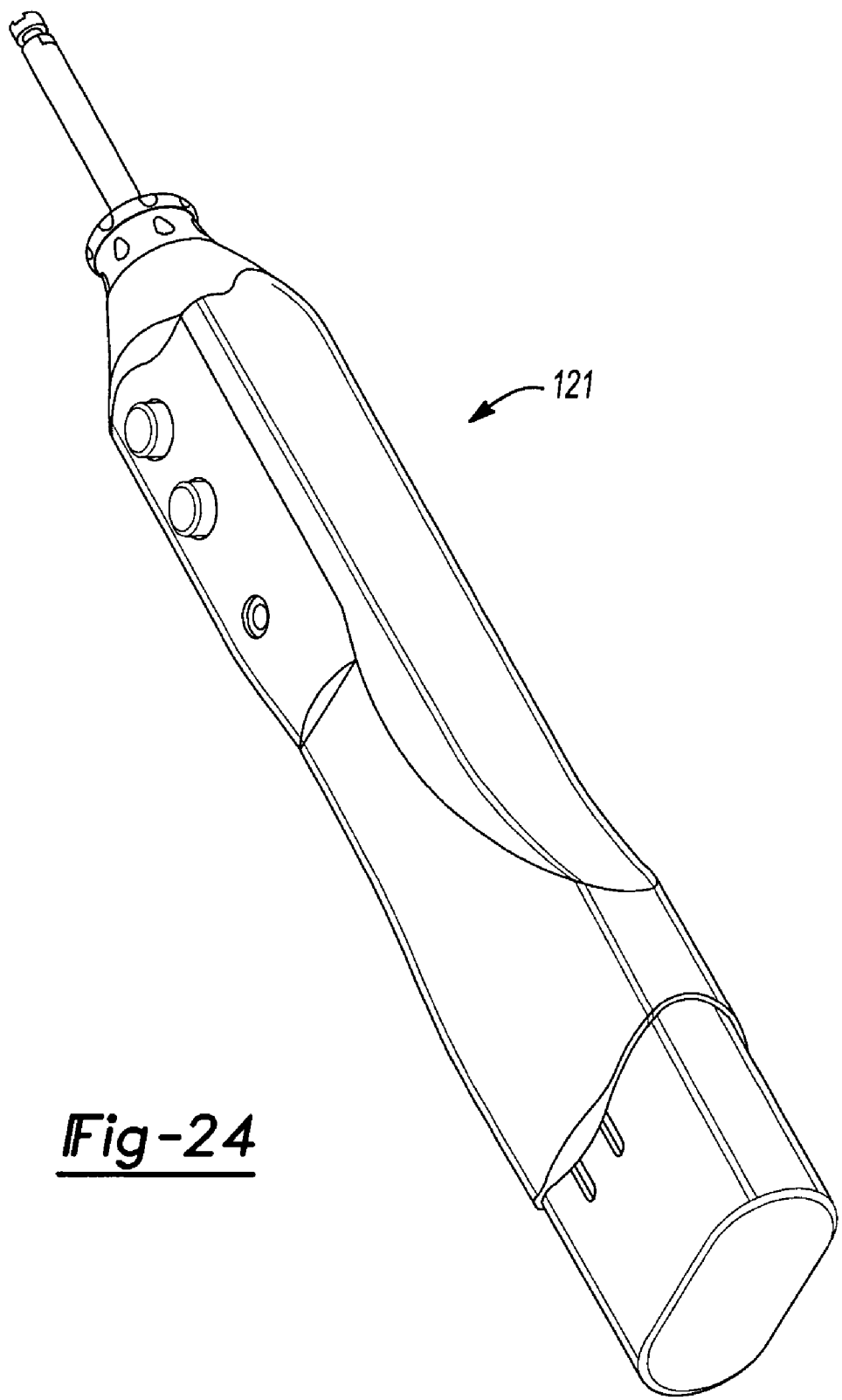
FIG. 24 is a perspective view of a power driver.

Alternatively, shaft 56 may be coupled to a power driver 121, as seen in FIG. 24. An exemplary power driver 121 may be Walter Lorenz Surgical Power Driver (part number 50-1000) (available from Walter Lorenz Surgical, Inc. of Jacksonville, Fla., U.S.A.). This arrangement may provide the same advantages of shaft 56 in a powered-drive arrangement.

In operation, a first fastener 12 may be urged into opening 82. It should be understood that while operation is described with reference to fastener 12, similar operation may be appropriate for the other fasteners described in the disclosure as well. Flats 38 on first fastener post 18 may be generally aligned with flats 99 on generally hollow portion 66. Once aligned, second end 34 of post 18 may be urged inward until it contacts pins 100. After contact with pins 100 is made, as fastener 12 is urged further inward, pins 100 are displaced radially outwardly through an engagement with sloped surface 49 against the force of outer ring member 102. As fastener 12 is forced into the generally hollow portion 66, pins 100 may engage recessed portion 43 of retaining feature 42 once pins 100 pass wall 46. Engagement with recessed portion 43 may generally allow pins 100 to once again travel radially inwardly due to the bias of outer ring member 102. Pins 100 may then be trapped between walls 44, 46 of retaining feature 42, generally preventing fastener 12 from falling out of driver 14. As post 18 is forced into generally hollow portion 66, protrusions 88 may generally engage recesses 30, coupling fastener 12 and driver 14 in a driving engagement. Stepped portions 87, 89, 91 may provide additional engagement between driver 14 and a fastener such as fastener 121 (seen in FIG. 16). More specifically, stepped portion 91 may extend into recesses 311 in fastener 121. Alternatively, if the fastener being used does not include recesses 30, such as fastener 12a (see FIG. 5), protrusions 88 may generally abut upper surface 22. In this configuration, fastener 12a can be in driving engagement with shaft 56 through engagement between fastener flats 38 and shaft flats 99.

Once fixed in the driving engagement, fastener 12 may be applied to a desired structure. When fastener 12 is sufficiently secured, head 16 may be removed from engagement with both driver 14 and post 18. This removal may occur by rocking driver 14, resulting in head 16 of fastener 12 breaking off from post 18 at breakaway connection 40.

Once post 18 is separated from head 16 of fastener 12, it may be retained by driver 14 through pins 100 being captured between walls 44, 46. The post 18 may then be forced into the generally hollow portion 66 of driver 14. This may be accomplished in a variety of ways. A first way may include pushing the post 18 inward with any suitable object with sufficient force to urge pins 100 outward along the sloped surface of wall 44, allowing wall 44, and eventually the entire post 18, to pass pins 100. Alternatively, a second fastener 12 may be used to urge post 18 inward. The second end 34 of post 18 may be urged inward against the previous post 18 until the previous post 18 is forced past pins 100. Once in this position, second fastener 12 may be urged inward until it contacts pins 100. The procedure above may then be repeated and the second fastener 12 may be placed in driving engagement with driver 14.

This process may allow fasteners to be quickly and easily coupled to driver 14. It also may allow posts 18 to be easily retained during procedures, resulting in convenient tracking of parts. When desired, shaft 56 may be removed from handle 62 by axially sliding the gripping portion 110, as previously discussed. Plug 101 may be removed from second end 96 and posts 18 can be emptied from within. The number of posts 18 contained within shaft 56 at any given time can be readily determined due to apertures 72. Apertures 72 may allow visual inspection of the number of posts 18 contained within shaft 56 without the need to remove the shaft 56. After posts 18 are removed, driver 14 may be sterilized and reused. Alternatively, driver 14 may be a disposable unit.

Figure 25:
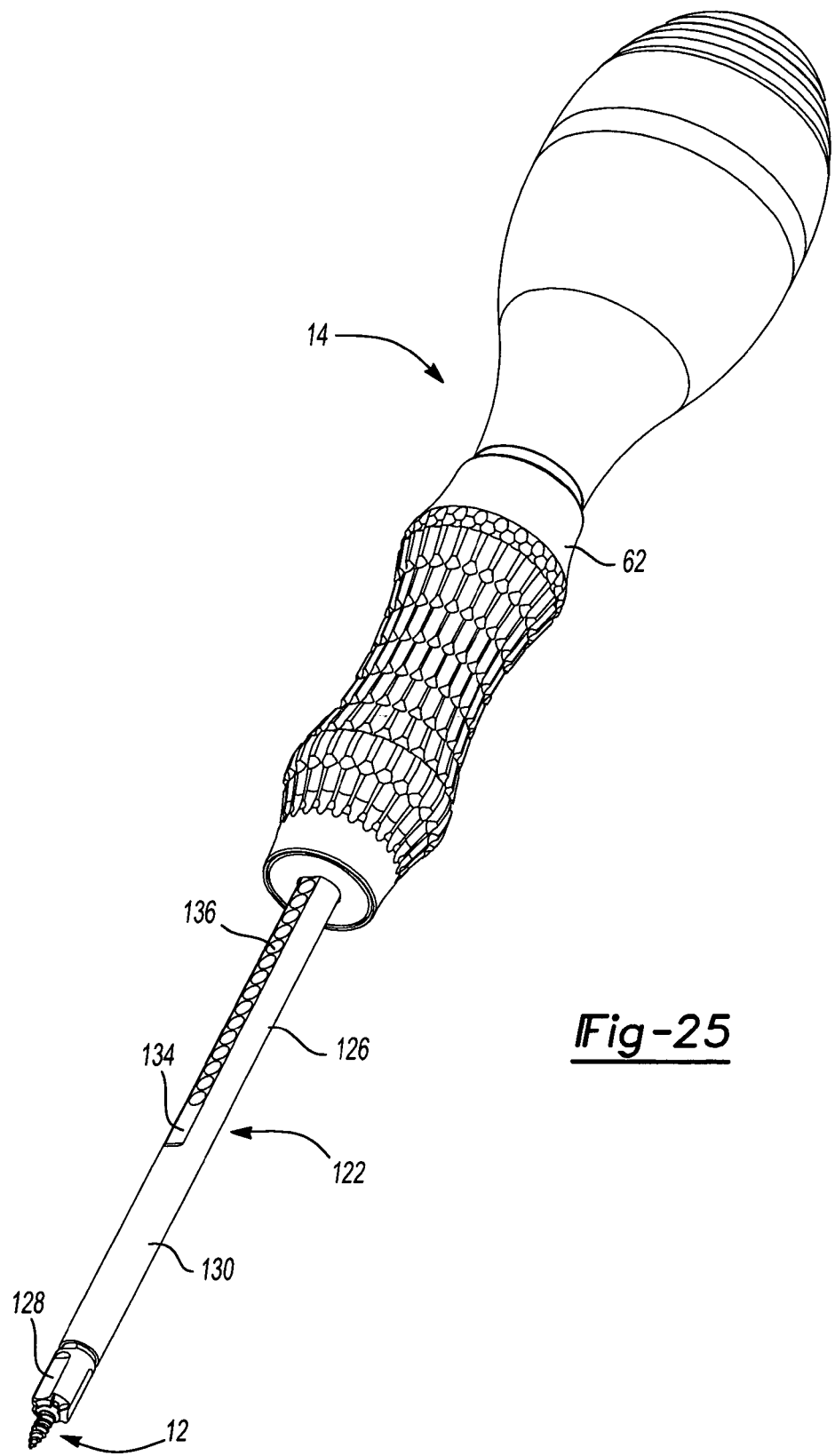
FIG. 25 is a perspective view of an additional driver assembly.
Figure 26:
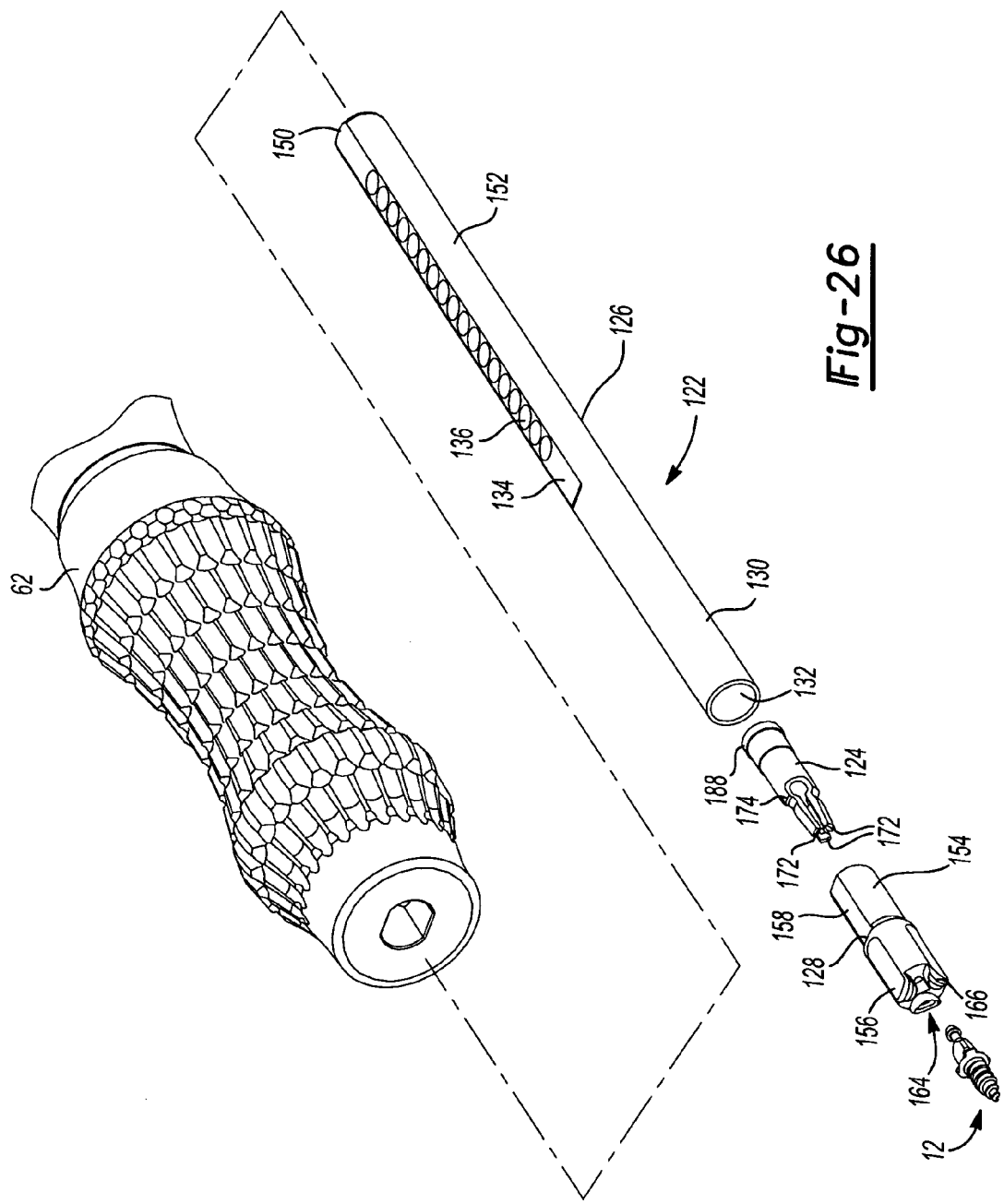
FIG. 26 is an exploded view of the driver assembly of FIG. 25.
Figure 27:
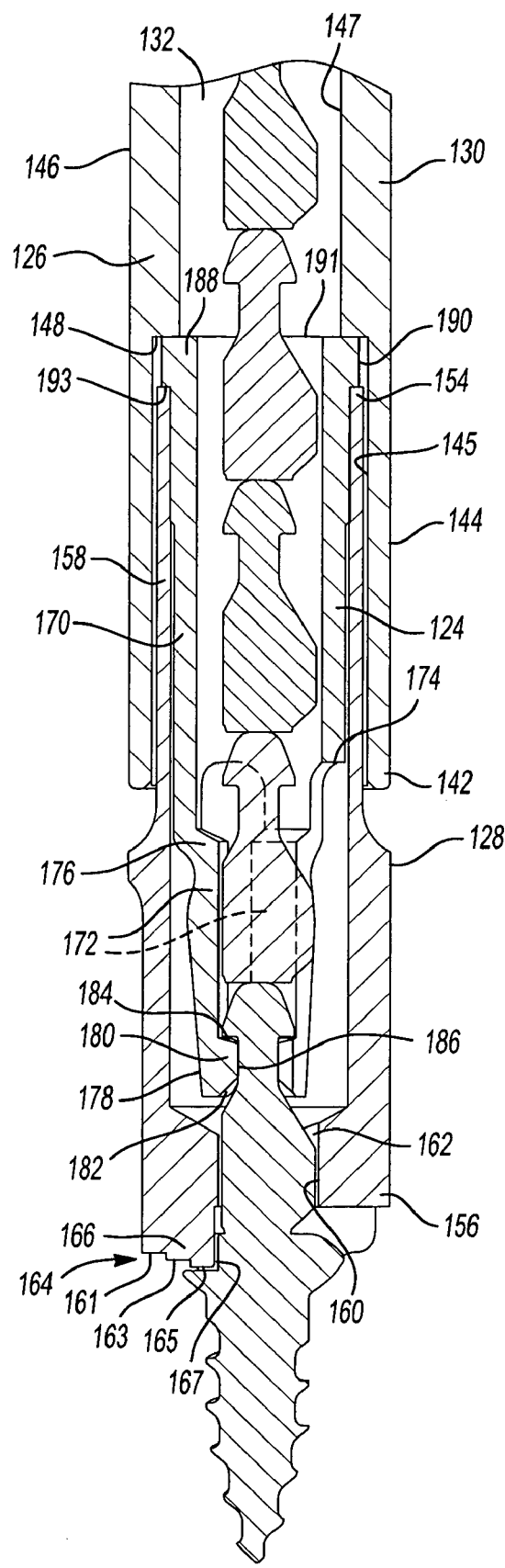
FIG. 27 is a fragmentary sectional view of the driver assembly shown in FIG. 25.

An additional shaft 122 and retaining member 124 are shown in FIGS. 25-27. The shaft 122 may be adjustably and removably coupled to handle 62 or power driver 121 in a manner similar to that described above regarding shaft 56. The shaft 122 may include first and second portions 126, 128. Each of which may be formed from a generally rigid material, such as stainless steel. Shaft 122 and retaining member 124 may be disposable members and discarded once removed from handle 62. Alternatively, shaft 122 may be reusable once sterilized.

The first portion 126 of shaft 122 may include a generally cylindrical body portion 130 and a generally hollow portion 132. The body portion 130 may include a series of flats 134, similar to flats 68. The flats 134 may include a series of dimples 136, similar to dimples 70, for engagement with handle 62, as described above regarding flats 68 and dimples 70. The body portion 130 may further include a series of apertures (not shown) extending radially therethrough and into the generally hollow portion 132, similar to apertures 72.

A first end portion 144 of body portion 130 may be located near first end 142. The main portion 146 of body portion 130 may have an inner diameter greater than a maximum diameter of post 18. The first end portion 144 may have an inner diameter greater than the inner diameter of the main portion 146 of body portion 130. A generally flat ledge 148 may be disposed between inner surfaces 145 of first end portion 144 and inner surface 147 of main portion 146.

A second end portion 152 of body portion 130 may be located near second end 150. The second end portion 152 may have an inner diameter less than the inner diameter of the main portion 146 of body portion 130. The inner diameter of second end portion 152 may also be less than a maximum diameter of post 18.

The second portion 128 may include first and second ends 154, 156. A first end portion 158 may be located near first end 154. First end portion 158 may be generally located within first end portion 144 of body portion 130. First end portion 158 may be retained within body portion 130 through an interference fit engagement.

The second end 156 may include a centrally disposed opening 160. The opening 160 may have a triangular cross-section similar to post 18. A series of flats 162 may be located within opening 160 generally corresponding to flats 38 on post 18. Alternatively, different cross-sections may be used, as discussed regarding shaft 56. The second end 156 may further include a fastener-engaging portion 164. The fastener-engaging portion 164 may extend from the second end 156 and include a series of protrusions 166. An inner portion 167 of each protrusion 166 may have a generally arcuate shape. The arcuate shape of protrusions 166 may be generally similar to arcuate recesses 30 in fastener 12.

Protrusions 166 may be similar to protrusions 88 and may also additionally include a series of stepped portions 161, 163, 165 similar to stepped portions 87, 89, 91. Stepped portions 161, 163, 165 may provide additional engagement with a fastener such as fastener 121 (seen in FIG. 16). Alternatively, protrusions 166 may be a variety of other shapes, having different inner and outer portions similar to another specific fastener driving geometry. Alternatively, protrusions 166 may not engage any recesses 30, as discussed regarding shaft 56.

The retaining member 124 may include a generally cylindrical member 170 having a plurality of fingers 172 extending from a first end 174. Retaining member 124 may be formed from a variety of materials including stainless steel and medical grade plastic.

The fingers 172 may be radially inwardly offset from the generally cylindrical member 170. Fingers 172 may include first and second ends 176, 178. The first end 176 may be coupled to generally cylindrical member 170 and the second end 178 may be generally free. The second end 178 may include portions 180 that extend radially inwardly. These portions 180 may include front, rear and inner surfaces 182, 184, 186. The front and rear surfaces 182, 184 may be sloped and the inner surface 186 may be generally parallel to the longitudinal axis of shaft 122. The distance between inner surfaces 186 may be approximately equal to the diameter of the recessed portion 43 of fastener 12 when fingers 172 are not being acted upon by any outside force. Fingers 172 may be radially outwardly displaceable upon application of a predetermined force, discussed in greater detail below.

A second end 188 of retaining member 124 may include a radially outwardly extending portion 190 captured between first portion ledge 148 and first end 154 of second portion 128. Radially outwardly extending portion 190 may include an axially outward surface 191 and an axially inward surface 193. Axially outward surface 191 may generally abut ledge 148 of first portion 126. Axially inward surface 193 may generally abut first end 154 of second portion 128. Generally cylindrical member 170 of retaining member 124 may also be engaged with first end portion 158 of second portion 128 through an interference fit. The remainder of retaining member 124 may be located within second portion 128 as well, with fingers 172 extending towards opening 160.

Figure 28:
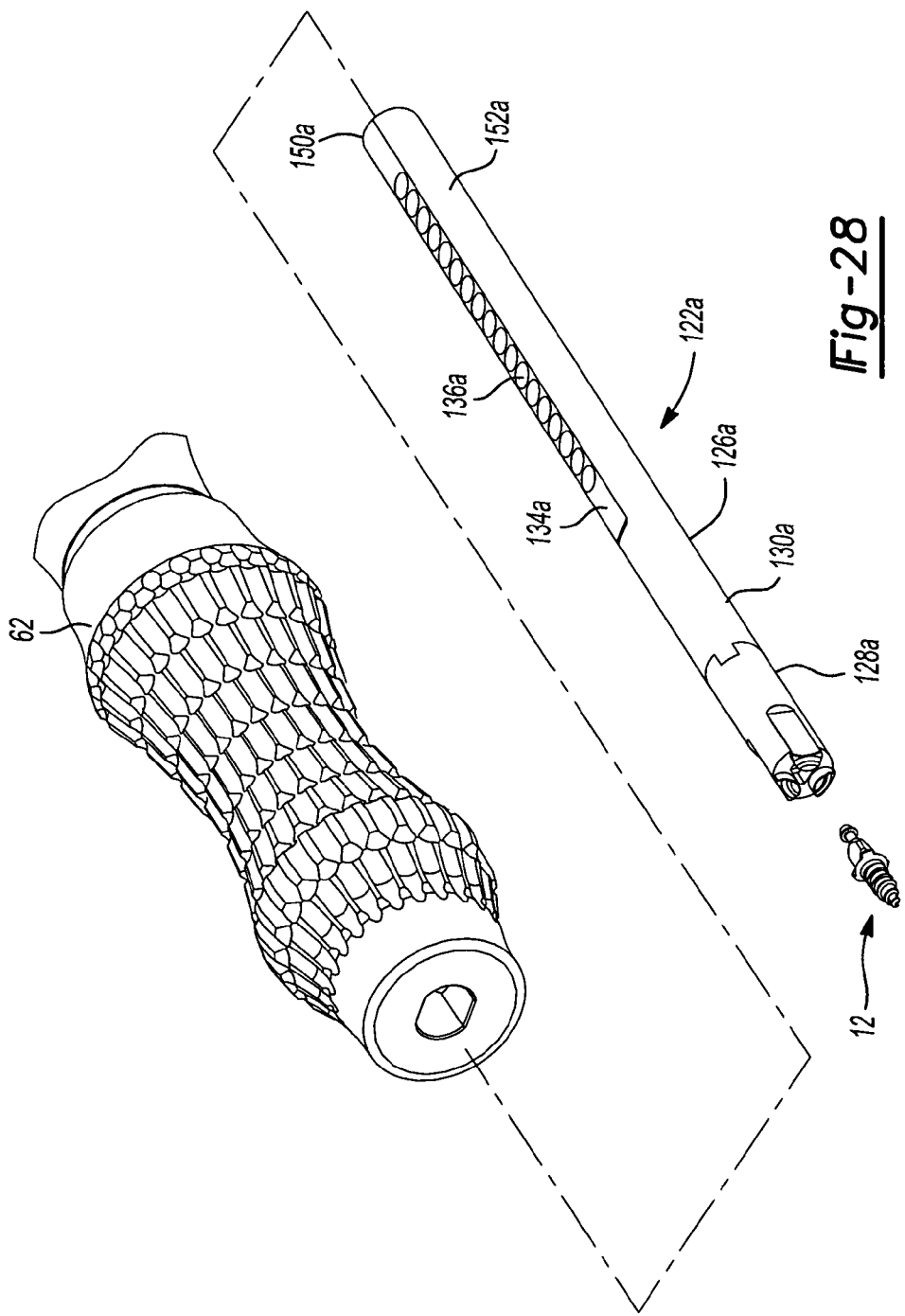
FIG. 28 is an exploded view of an additional driver assembly.
Figure 29:
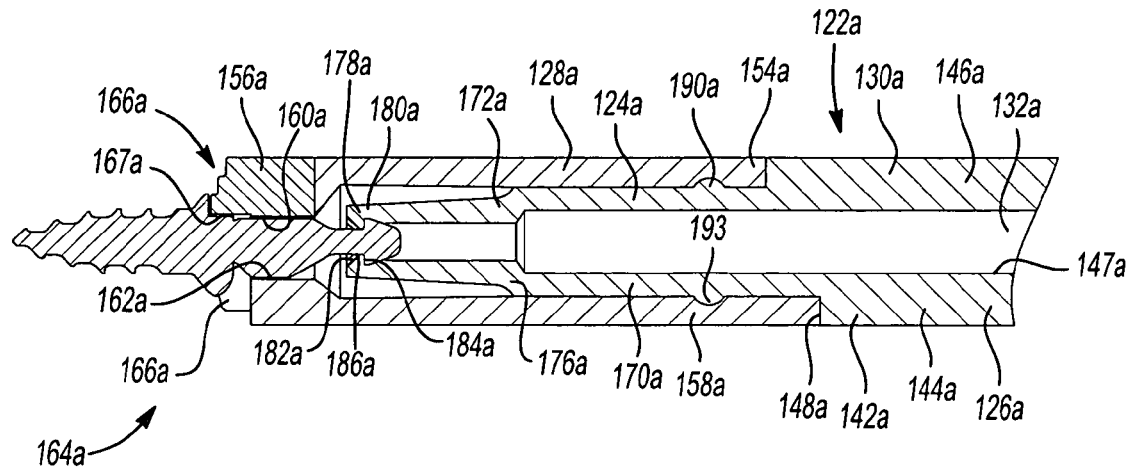
FIG. 29 is a fragmentary sectional view of the driver assembly shown in FIG. 28.

An additional shaft 122a having an integrally formed retaining member 124a is shown in FIGS. 28 and 29. Shaft 122a may be generally similar to shaft 122 in a variety of ways. Therefore, like reference numerals ending in "a" will be used for similar parts. The shaft 122a may be adjustably and removably coupled to handle 62 or power driver 121 in a manner similar to that described above regarding shaft 56. The shaft 122a may include first and second portions 126a, 128a. Each of which may be formed from a generally rigid material, such as stainless steel. Shaft 122a may be a disposable member and discarded once removed from handle 62. Alternatively, shaft 122a may be reusable once sterilized.

The first portion 126a of shaft 122a may include a generally cylindrical body portion 130a and a generally hollow portion 132a. The body portion 130a may include a series of flats 134a, similar to flats 68. The flats 134a may include a series of dimples 136a, similar to dimples 70, for engagement with handle 62, as described above regarding flats 68 and dimples 70. The body portion 130a may further include a series of apertures (not shown) extending radially therethrough and into the generally hollow portion 132a, similar to apertures 72.

A first end portion 144a of body portion 130a may be located near first end 142a. The body portion 130a may have an inner diameter greater than a maximum diameter of post 18. A generally flat ledge 148a may be disposed at first end 142a.

A second end portion 152a of body portion 130a may be located near second end 150a. The second end portion 152a may have an inner diameter less than the inner diameter of the main portion 146a of body portion 130a. The inner diameter of second end portion 152a may also be less than a maximum diameter of post 18.

The retaining member 124a may extend from first end 142a of body portion 130a. The retaining member 142a may include a generally cylindrical member 170a having a plurality of fingers 172a formed therein. The generally cylindrical member 170a may have an outer diameter less than the outer diameter of body portion 130a.

The fingers 172a may be radially inwardly offset from the generally cylindrical member 170a. Fingers 172a may include first and second ends 176a, 178a. The first end 176a may be coupled to generally cylindrical member 170a and the second end 178a may be generally free. The second end 178a may include portions 180a that extend radially inwardly. These portions 180a may include front, rear and inner surfaces 182a, 184a, 186a. The front and rear surfaces 182a, 184a may be sloped and the inner surface 186a may be generally parallel to the longitudinal axis of shaft 122a. The distance between inner surfaces 186a may be approximately equal to the diameter of the recessed portion 43 of fastener 12 when fingers 172a are not being acted upon by any outside force. Fingers 172a may be radially outwardly displaceable upon application of a predetermined force, discussed in greater detail below.

The generally cylindrical portion 170a of retaining member 124a may include a radially outwardly extending portion 190a, discussed in greater detail below. Radially outwardly extending portion 190a may include a generally continuous protrusion or a series of discrete protrusions.

The second portion 128a may include first and second ends 154a, 156a. A first end portion 158a may be located near first end 154a. First end portion 158a may generally surround cylindrical portion 130a. First end 154a may generally abut ledge 148a. First end portion 158a may have a recess 193 on an inner portion. Recess 193 may be generally continuous or a series of discrete recesses. Recess 193 may receive radially outwardly extending portion 190a, resulting in a snap-fit engagement between first portion 126a and second portion 128a.

The second end 156a may include a centrally disposed opening 160a. The opening 160a may have a triangular cross-section similar to post 18. A series of flats 162a may be located within opening 160a generally corresponding to flats 38 on post 18. Alternatively, different cross-sections may be used, as discussed regarding shaft 56. The second end 156a may further include a fastener-engaging portion 164a. The fastener-engaging portion 164a may extend from the second end 156a and include a series of protrusions 166a generally similar to protrusions 166. An inner portion 167a of each protrusion 166a may have a generally arcuate shape. The arcuate shape of protrusions 166a may be generally similar to arcuate recesses 30 in fastener 12. Alternatively, protrusions 166a may be a variety of other shapes, having different inner and outer portions similar to another specific fastener driving geometry. Alternatively, protrusions 166a may not engage any recesses 30, as discussed regarding shaft 56.

Figure 31:
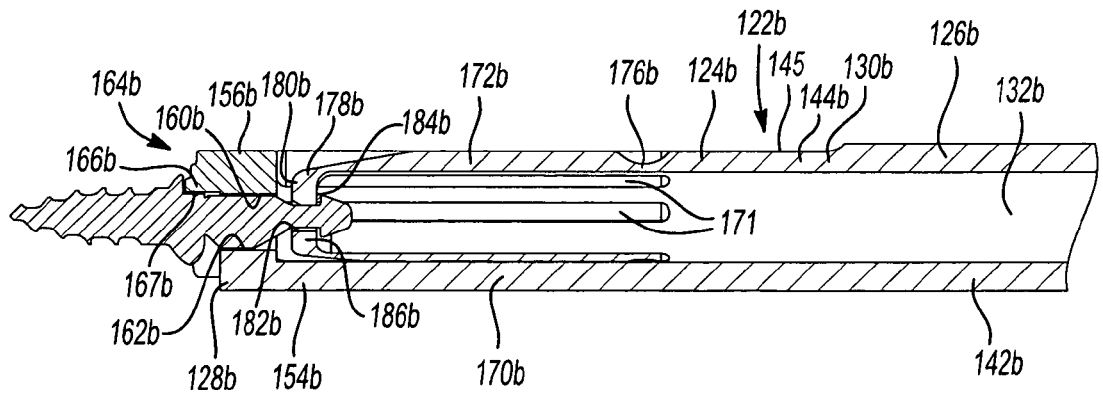
FIG. 31 is a fragmentary sectional view of the driver assembly shown in FIG. 30.
Figure 30:
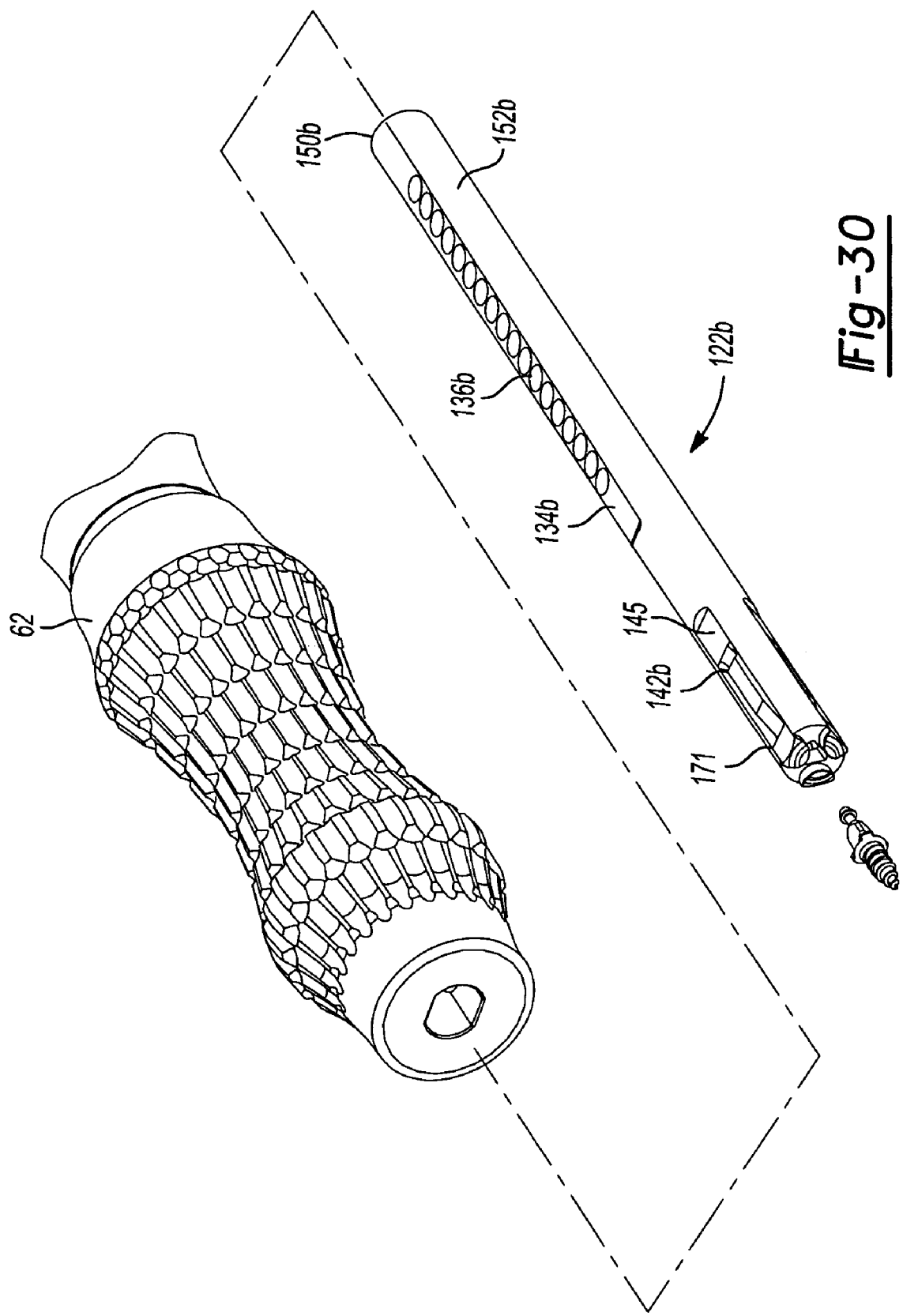
FIG. 30 is an exploded view of an additional driver assembly.

An additional shaft 122b may be formed as a single piece, having an integrally formed retaining member 124b as shown in FIGS. 30 and 31. Shaft 122b may be generally similar to shaft 122 in a variety of ways. Therefore, like reference numerals ending in "b" will be used for similar parts. The shaft 122b may be adjustably and removably coupled to handle 62 or power driver 121 in a manner similar to that described above regarding shaft 56. Shaft 122b may generally have a first portion 126b, a second portion 128b and a retaining portion 124b generally disposed between first and second portions 126b, 128b. Shaft 122b may be formed from a generally rigid material, such as stainless steel. Shaft 122b may be a disposable member and discarded once removed from handle 62. Alternatively, shaft 122b may be reusable once sterilized.

The first portion 126b of shaft 122b may include a generally cylindrical body portion 130b and a generally hollow portion 132b. The body portion 130b may include a series of flats 134b, similar to flats 68. The flats 134b may include a series of dimples 136b, similar to dimples 70, for engagement with handle 62, as described above regarding flats 68 and dimples 70. The body portion 130b may further include a series of apertures (not shown) extending radially therethrough and into the generally hollow portion 132b, similar to apertures 72.

A first end portion 144b of body portion 130b may be located near first end 142b. The body portion 130b may have an inner diameter greater than a maximum diameter of post 18. Flats 145 may be located on first end portion 144b.

A second end portion 152b of body portion 130b may be located near second end 150b. The second end portion 152b may have an inner diameter less than the inner diameter of the body portion 130b. The inner diameter of second end portion 152b may also be less than a maximum diameter of post 18.

The retaining portion 124b may extend from first end 142b of body portion 130b. The retaining portion 124b may include a generally cylindrical portion 170b. The generally cylindrical portion 170b may include windows 171 therein. A plurality of fingers 172b may extend from the first end 142b of body portion 130b. The fingers 172b may be generally located within windows 171.

The fingers 172b may be radially inwardly offset from the generally cylindrical portion 170b. Fingers 172b may include first and second ends 176b, 178b. The first end 176b may be coupled to generally cylindrical member 170b and the second end 178b may be generally free. The second end 178b may include portions 180b that extend radially inwardly. These portions 180b may include front, rear and inner surfaces 182b, 184b, 186b. The inner surface 182b may be sloped. Rear surface 184b may extend generally perpendicular to the longitudinal axis of shaft 122b. Inner surface 186b may be generally parallel to the longitudinal axis of shaft 122b. The distance between inner surfaces 186b may be approximately equal to the diameter of the recessed portion 43 of fastener 12 when fingers 172b are not being acted upon by any outside force. Fingers 172b may be radially outwardly displaceable upon application of a predetermined force, discussed in greater detail below.

The second portion 128b may include first and second ends 154b, 156b. Second portion 128b may generally extend from cylindrical portion 170b at first end 154b.

The second end 156b may include a centrally disposed opening 160b. The opening 160b may have a triangular cross-section similar to post 18. A series of flats 162b may be located within opening 160b generally corresponding to flats 38 on post 18. Alternatively, different cross-sections may be used, as discussed regarding shaft 56. The second end 156b may further include a fastener-engaging portion 164b. The fastener-engaging portion 164b may extend from the second end 156b and include a series of protrusions 166b generally similar to protrusions 166. An inner portion 167b of each protrusion 166b may have a generally arcuate shape. The arcuate shape of protrusions 166b may be generally similar to arcuate recesses 30 in fastener 12. Alternatively, protrusions 166b may be a variety of other shapes, having different inner and outer portions similar to another specific fastener driving geometry. Alternatively, protrusions 166b may not engage any recesses 30, as discussed regarding shaft 56.

For simplicity, operation of shaft 122 will be discussed with the understanding that shafts 122a and 122b (shown in FIGS. 28-31) operate similarly. In operation, a first fastener 12 may be urged into opening 160. Flats 38 on first fastener post 18 may be generally aligned with flats 162 on opening 160. Once aligned, second end 34 of post 18 may be urged inward until it contacts fingers 172. After contact with fingers 172 is made, as fastener 12 is urged further inward, fingers 172 are displaced radially outwardly through an engagement between finger inner surface 182 and fastener sloped surface 49. As fastener 12 is forced into opening 160, finger portions 180 may engage recessed portion 43 of retaining feature 42 once finger portions 180 pass wall 46. Engagement with recessed portion 43 may generally allow fingers 172 to once again travel radially inwardly to their normal positions. Finger portions 180 are then trapped between walls 44, 46 of retaining feature 42, generally preventing fastener 12 from falling out of shaft 122. As post 18 is forced through opening 160, protrusions 166 may generally engage recesses 30, coupling fastener 12 and shaft 122 in driving engagement.

Once fixed in the driving engagement, fastener 12 may be applied to a desired structure. When fastener 12 is sufficiently secured, fastener head 16 may be removed from engagement with both shaft 122 and post 18. This removal may occur by rocking shaft 122, resulting in head 16 of fastener 12 breaking off from post 18 at breakaway connection 40.

Once post 18 is separated from head 16 of fastener 12, it may be retained by shaft 122 through finger portions 180 being captured between walls 44, 46. Post 18 may then be forced past finger portions 180 and into generally hollow portion 132. This may be accomplished in a number of ways. A first way may include pushing post 18 inward with any suitable object with sufficient force to urge fingers 172 outward along the sloped surface of wall 44, allowing wall 44 to pass finger portions 180. Alternatively, a second fastener 12 may be used to urge post 18 inward. The second end 34 of post 18 may be urged inward against previous post 18 until previous post 18 is forced past finger portions 180. Once in this position, second fastener 12 may be urged inward until it contacts fingers 172. The procedure above may then be repeated and the second fastener 12 may be placed in driving engagement with driver 14.

This process may allow fasteners to be quickly and easily coupled to shaft 122. It may also allow posts 18 to be easily retained during procedures, resulting in convenient tracking of parts. When desired, shaft 122 and retaining member 124 may be removed from handle 62. Shaft 122 and retaining member 124 may be discarded when finished as a disposable unit.

Figure 32:
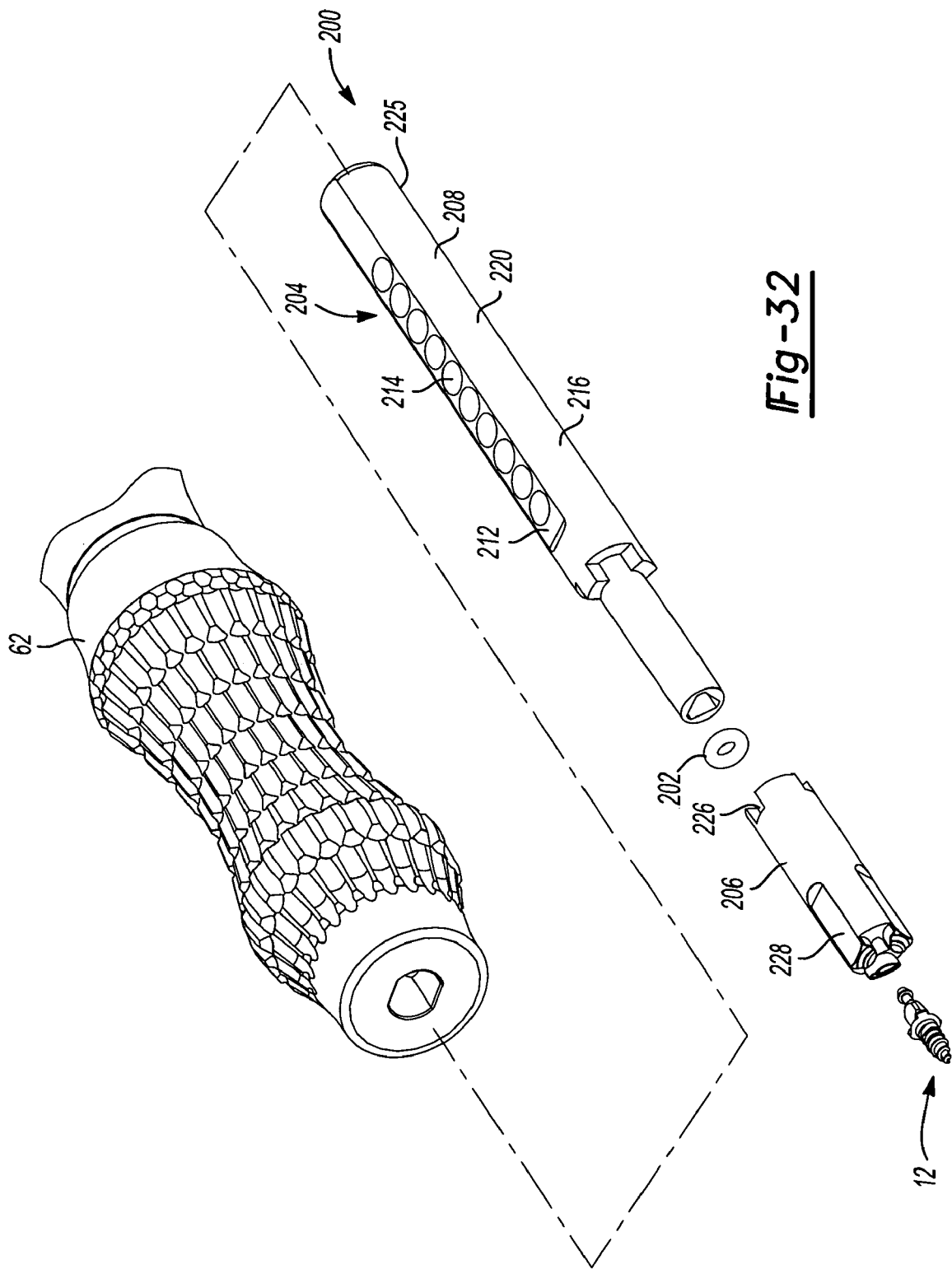
FIG. 32 is an exploded view of an additional driver assembly.
Figure 33:
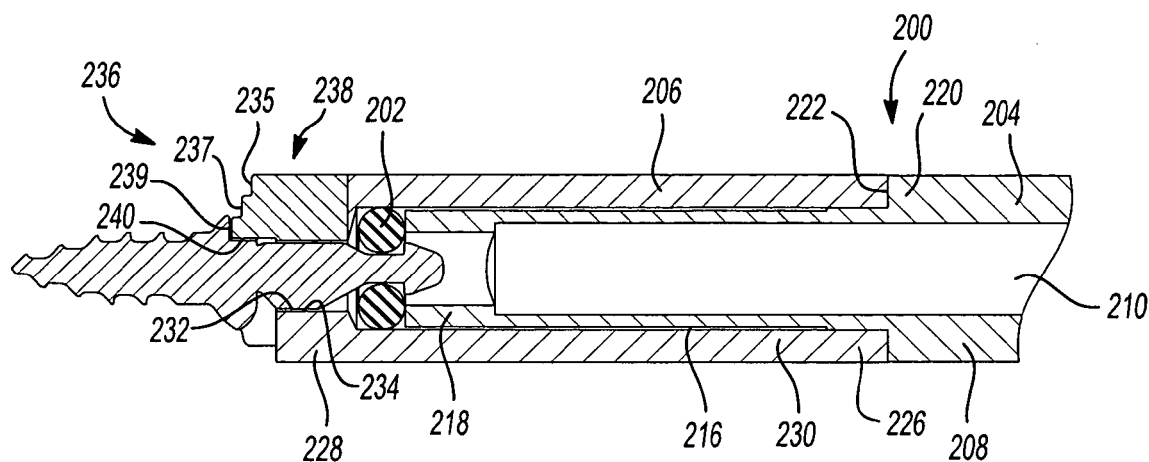
FIG. 33 is a fragmentary sectional view of the driver assembly shown in FIG. 32.

An additional shaft 200 and retaining member 202 are shown in FIGS. 32 and 33. The shaft 200 may be adjustably and removably coupled to handle 62 or power driver 121 in a manner similar to that described above regarding shaft 56. The shaft 200 may include first and second portions 204, 206. Each of which may be formed from a generally rigid material, such as stainless steel. Shaft 200 and retaining member 202 may be disposable members and discarded once removed from handle 62. Alternatively, shaft 200 may be reusable once sterilized.

The first portion 204 of shaft 200 may include a generally cylindrical body portion 208 and a generally hollow portion 210. The body portion 208 may include a series of flats 212, similar to flats 68. The flats 212 may include a series of dimples 214, similar to dimples 70, for engagement with handle 62, as described above regarding flats 68 and dimples 70. The body portion 208 may further include a series of apertures (not shown) extending radially therethrough and into the generally hollow portion 210, similar to apertures 72.

A first end portion 216 of body portion 208 may be located near first end 218. The main portion 220 of body portion 208 may have an inner diameter greater than a maximum diameter of post 18. The first end portion 216 may have an inner diameter generally equal to the inner diameter of the main portion 220. The outer diameter of first end portion 216 may be less than the outer diameter of the main portion 220. A generally flat ledge 222 may be disposed between first end portion 216 and main portion 220.

A second end portion 224 of body portion 208 may be located near second end 226. The second end portion 224 may have an inner diameter less than the inner diameter of the main portion 220 of body portion 208. The inner diameter of second end portion 224 may also be less than a maximum diameter of post 18.

The second portion 206 may include first and second ends 226, 228. A first end portion 230 may be located near first end 226. First end portion 230 may generally surround first end portion 216 of body portion 208. First end portion 216 may be retained within second portion 206 through an interference fit engagement.

The second end 228 may include a centrally disposed opening 232. The opening 232 may have a triangular cross-section similar to post 18. A series of flats 234 may be located within opening 232 generally corresponding to flats 38 on post 18. Alternatively, different cross-sections may be used, as discussed regarding shaft 56. The second end 228 may further include a fastener-engaging portion 236. The fastener-engaging portion 236 may extend from the second end 228 and include a series of protrusions 238. An inner portion 240 of each protrusion 238 may have a generally arcuate shape. The arcuate shape of protrusions 238 may be generally similar to arcuate recesses 30 in fastener 12.

Protrusions 238 may be similar to protrusions 88 and may also additionally include a series of stepped portions 235, 237, 239 similar to stepped portions 87, 89, 91. Stepped portions 235, 237, 239 may provide additional engagement with a fastener such as fastener 121 (seen in FIG. 16). Alternatively, protrusions 238 may be a variety of other shapes, having different inner and outer portions similar to another specific fastener driving geometry. Alternatively, protrusions 238 may not engage any recesses 30, as discussed regarding shaft 56.

Figure 34:
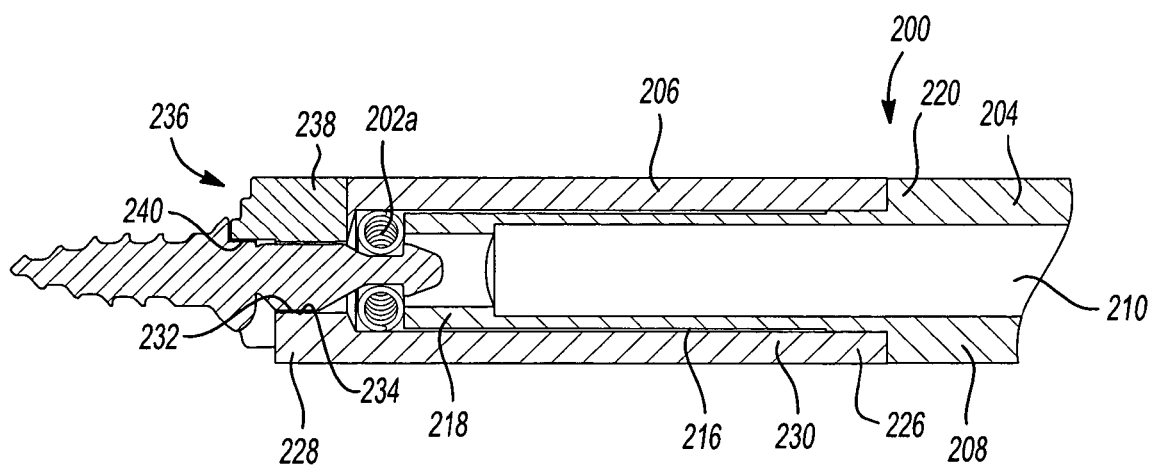
FIG. 34 is a fragmentary sectional view of the driver assembly shown in FIG. 32 with an alternate retaining member.

The retaining member 202 may be a generally flexible ring. Retaining member 202 may be formed from a variety of materials. Retaining member 202 is shown as a silicon o-ring. FIG. 34 shows an alternative retaining member 202a. Retaining member 202a may generally be a garter spring.

Retaining member 202, 202a may have an outer diameter generally equal to the inner diameter of second portion 206. The inner diameter of retaining member 202, 202a may be similar to the outer diameter of recessed portion 43 on post 18 when not acted upon by an outside force. While retaining member 202, 202a has been shown as an o-ring and as a garter spring, it is understood that a variety of other flexible rings may be used as well.

In operation, a first fastener 12 may be urged into opening 232. It should be understood that while operation is described with reference to fastener 12, similar operation may be appropriate for the other fasteners described in the disclosure as well. Flats 38 on first fastener post 18 may be generally aligned with flats 234 within opening 232. Once aligned, second end 34 of post 18 may be urged inward until it contacts retaining member 202. After contact with retaining member 202 is made, as fastener 12 is urged further inward, retaining member 202 is displaced radially outwardly through an engagement with sloped surface 49 against the force of retaining member 202. As fastener 12 is forced into the generally hollow portion 210, retaining member 202 may engage recessed portion 43 of retaining feature 42 once retaining member 202 passes wall 46. Engagement with recessed portion 43 may generally allow retaining member 202 to once again travel radially inwardly due to the bias of retaining member 202. Retaining member 202 may then be trapped between walls 44, 46 of retaining feature 42, generally preventing fastener 12 from falling out of shaft 200. As post 18 is forced into generally hollow portion 210, protrusions 238 may generally engage recesses 30, coupling fastener 12 and shaft 200 in a driving engagement. Alternatively, if the fastener being used does not include recesses 30, such as fastener 12a (see FIG. 5), protrusions 238 may generally abut upper surface 22. In this configuration, fastener 12a can be in driving engagement with shaft 200 through engagement between fastener flats 38 and shaft flats 234.

Once fixed in the driving engagement, fastener 12 may be applied to a desired structure. When fastener 12 is sufficiently secured, it may be removed from engagement with both shaft 200 and post 18. This removal may occur by rocking shaft 200, resulting in head 16 of fastener 12 breaking off from post 18 at breakaway connection 40.

Once post 18 is separated from head 16 of fastener 12, it may be retained by shaft 200 through retaining member 202 being captured between walls 44, 46. The post 18 may then be forced into the generally hollow portion 210 of shaft 200. This may be accomplished in a variety of ways. A first way may include pushing the post 18 inward with any suitable object with sufficient force to urge retaining member 202 outward along the sloped surface of wall 44, allowing wall 44, and eventually the entire post 18, to pass retaining member 202. Alternatively, a second fastener 12 may be used to urge post 18 inward. The second end 34 of post 18 may be urged inward against the previous post 18 until the previous post 18 is forced past retaining member 202. Once in this position, second fastener 12 may be urged inward until it contacts retaining member 202. The procedure above may then be repeated and the second fastener 12 may be placed in driving engagement with shaft 200.

This process may allow fasteners to be quickly and easily coupled to shaft 200. It also may allow posts 18 to be easily retained during procedures, resulting in convenient tracking of parts. When desired, shaft 200 may be removed from handle 62. Shaft 200 and retaining member 202 may be discarded when finished as a disposable unit. Alternatively, shaft 200 and retaining member 202 may be reused after sterilization.

Figure 35:
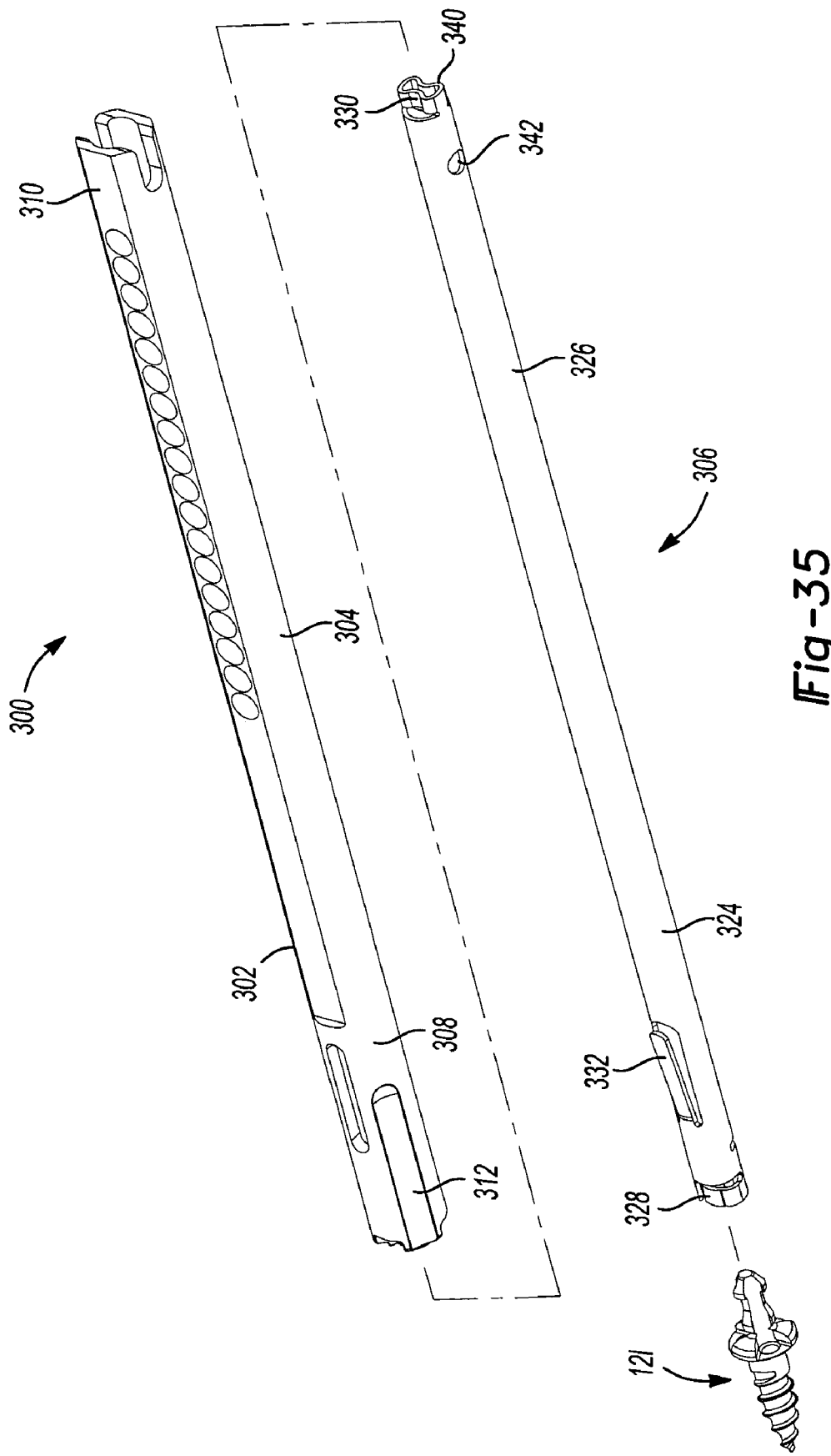
FIG. 35 is an exploded perspective view of an additional driver assembly.
Figure 36:
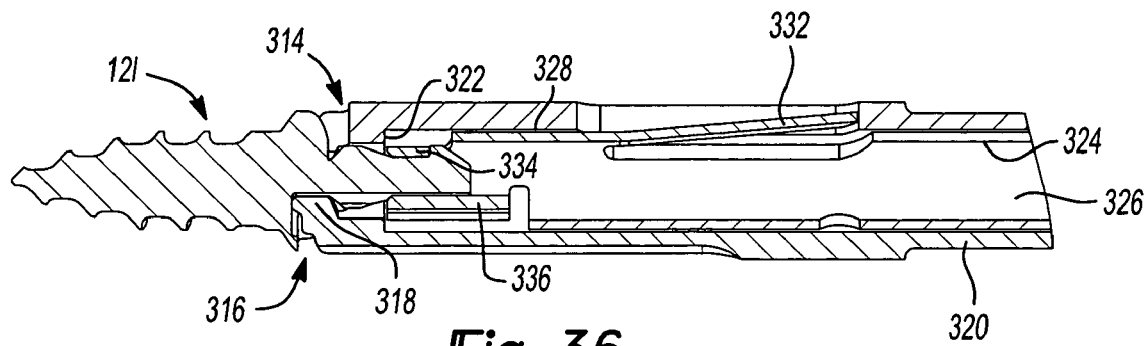
FIG. 36 is a fragmentary section view of the driver assembly of FIG. 35.
Figure 37:
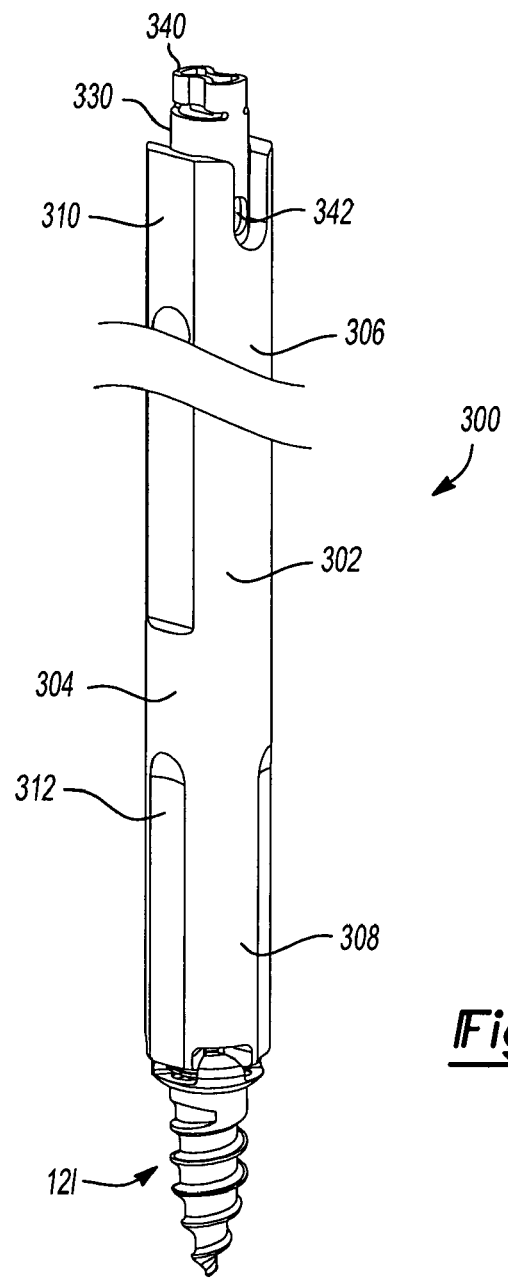
FIG. 37 is a fragmentary perspective view of the driver assembly of FIG. 35.

As seen in FIGS. 35-37, an alternate shaft 300 may include a generally cylindrical body portion 302 having a generally hollow center portion 304 with an insert 306 contained therein. Shaft 300 may be adjustably and removably coupled to handle 62 or power driver 121 in a manner similar to that described above regarding shaft 56. Body portion 302 may include first and second ends 308, 310 and a slot 312 disposed therebetween. First end 308 may include a fastener engaging portion 314 having protrusions 316 similar to protrusions 88, discussed above. A protrusion 318 may extend radially inwardly from an inner wall 320 of center portion 304 near first end 308. First end 308 may further include a reduced diameter compared to the remainder of center portion 304, forming a stepped portion 322.

Insert 306 may include a body 324 having a generally hollow center portion 326. Insert body 324 may include first and second ends 328, 330. First end 328 may generally abut stepped portion 322 and second end 330 may extend beyond second end 310 of body portion 302. Insert body 324 may include a radially outwardly extending tab 332 located near first end 328 and engaged with slot 312, preventing relative rotation and axially outward translation between insert 306 and body portion 302. Insert body 324 may further include a fastener retaining member 334 and a fastener alignment member 336 at first end 328.

Fastener retaining member 334 may be in the form a circumferentially extending tab member biased radially inwardly toward a center portion 326. Retaining member 334 may generally act as a leaf spring to provide engagement with a fastener, as discussed below. Alignment member 336 may include an axially extending protrusion having a radially inward extent which may conform to a specific fastener geometry. In the example shown in FIGS. 35-37, alignment member 336 is generally arcuate for engagement with a fastener, as discussed below.

Second end 330 may include a stop member 340 formed thereon. Stop member 340 may form a reduced opening area at second end 330, generally retaining a fastener portion within insert 306 as discussed below. Second end 330 may also include an aperture 342 extending radially therethrough for visual indication of contents of insert 306. Second end 330 may also extend axially beyond shaft second end 310, allowing for removal of insert 306 and disposal thereof, as insert 306 may be a disposable member.

In operation, a fastener, such as fastener **12*l* seen in FIG. 16, may be inserted into insert 306 of shaft 300 near fastener engaging portion 314. Recesses 35*l* in post 18*l* of fastener 12*l* may be aligned with protrusion 318, thereby aligning protrusions 316 with recesses 30 in fastener 12*l*. Once aligned, second end 34*l* of post 18*l* may be urged inward until it contacts fastener retaining member 334. After contact with fastener retaining member 334 is made, as fastener 12*l* is urged further inward, fastener retaining member 334 is displaced radially outwardly due through an engagement with sloped surface 49*l*. As fastener 12*l* is forced into insert 306, fastener retaining member 334 may engage a recessed portion 43*l* of fastener 12*l*, generally retaining post 18*l* within insert 306. As post 18*l* is inserted into insert 306, protrusions 316 may generally engage recesses 30*l* providing a driving engagement therebetween, as discussed above regarding driver 14 and fastener 12**.

Fastener **12*l* may then be driven into an object and post 18*l* may be separated from head 16*l* in a manner similar to that discussed above regarding fastener 12. Once post 18*l* is separated from head 16*l*, it may be retained by fastener retaining member 334 through an engagement between fastener retaining member 334 and recessed portion 35*l*. Post 18*l* may then be forced into insert 306 past fastener retaining member 334 in a manner similar to those discussed above regarding fastener 12 and driver 14**.

Figure 38:
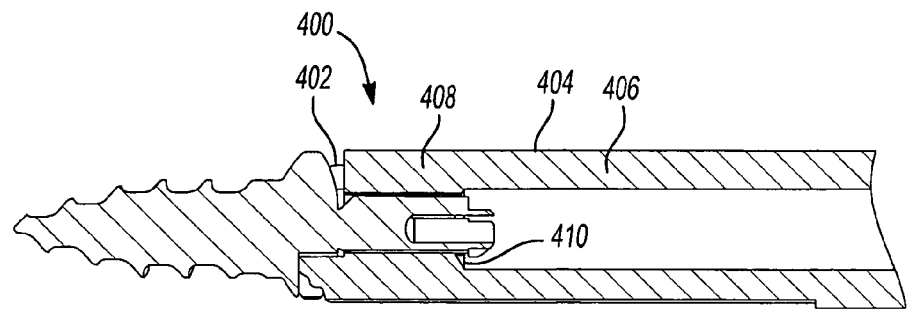
FIG. 38 is a fragmentary section view of an additional driver assembly.

As seen in FIG. 38, an alternate shaft 400 may include a fastener engaging portion 402 and a fastener retaining portion 404. Shaft 400 may be adjustably and removably coupled to handle 62 or power driver 121 in a manner similar to that described regarding shaft 56. Fastener engaging portion 402 may be generally similar to fastener engaging portion 46 described above. Fastener engaging portion 402 may include first and second portions 406, 408. Second portion 408 may have a diameter less than the diameter of first portion 406 forming a ledge 410 therebetween. Second portion 408 may be disposed between first portion 406 and fastener engaging portion 402.

In operation, when a fastener, such as fastener **12*p* or fastener 12*q* (seen in FIGS. 20 and 21), is placed in fastener retaining portion 404 it may be retained in engagement with fastener engaging portion 402. More specifically, end portions 47*p*, 47*q* may have a diameter greater than that of second portion 408 of fastener engaging portion 402 and less than that of first portion 406 of fastener engaging portion 402. Arms 37*p*, 37*q* may be flexed radially inwardly when fastener 12*p*, 12*q* is inserted into second portion 408 of fastener retaining portion 404. When end portions 47*p*, 47*q* are inserted into first portion 406 of fastener engaging portion 404, end portions 47*p*, 47*q* may return to their original shape having a diameter greater than the diameter of second portion 408. Walls 46*p*, 46*q* of fastener 12*p*, 12*q* may then engage ledge 410, preventing removal of post 18*p*, 18*q*** therefrom.

Figure 40:
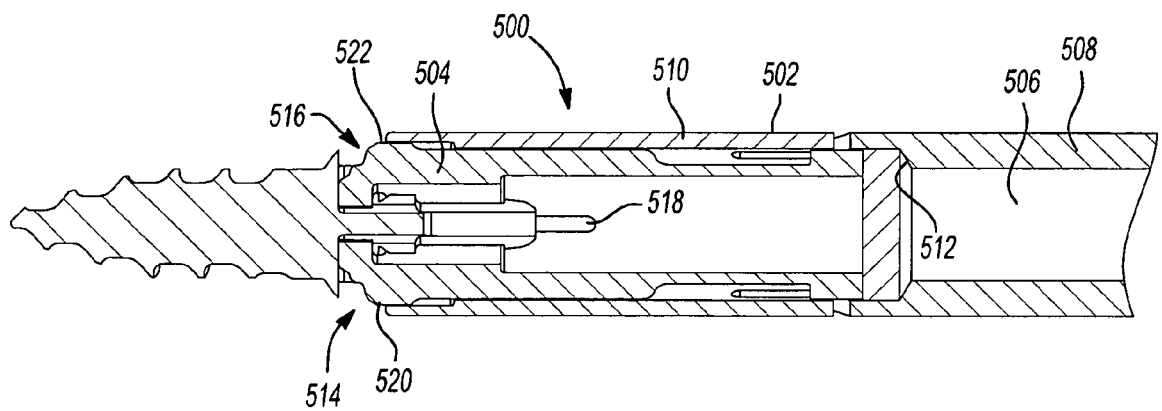
FIG. 40 is a fragmentary section view of the driver assembly of FIG. 39.
Figure 39:
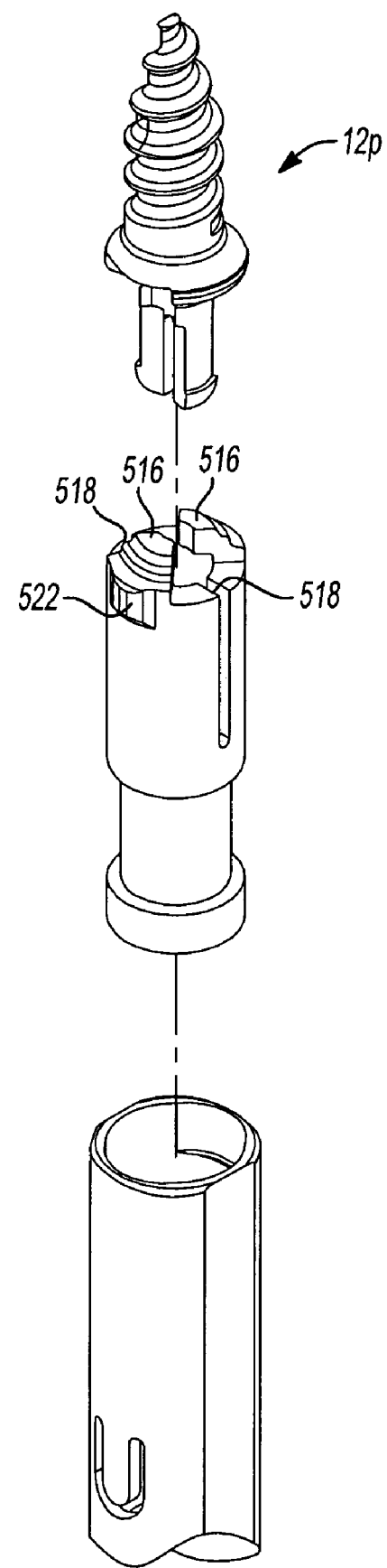
FIG. 39 is a fragmentary exploded perspective view of an additional driver assembly.

As seen in FIGS. 39 and 40, an alternate shaft 500 is shown. Shaft 500 may be adjustably and removably coupled to handle 62 or power driver 121 in a manner similar to that described above regarding shaft 56. Shaft 500 may include a main body 502 and an insert 504. Main body 502 may have a generally hollow center 506 having first and second portions 508, 510. First portion 508 may have a smaller inner diameter than second portion 510, forming a ledge 512 therebetween. Insert 504 may be contained within second portion 510.

Second portion 510 may include a fastener engaging portion 514 having two protrusions 516 generally similar to the protrusions 88*a* shown in FIG. 22. However, insert 504 may additionally include slots 518 extending from a central portion of insert 504 to fastener engaging portion 514. Fastener engaging portion 514 may additionally include first and second radially outwardly extending protrusions 520, 522 engaged with an inner surface of main body second portion 510.

Operation of shaft 500 may be generally similar to the operation of shaft 56 described above. However, due to the engagement between protrusions 520, 522 and main body 502, as well as slots 518, protrusions 516 may be biased radially inwardly, providing a radially inwardly biased engagement with a fastener.

The description is merely exemplary in nature and, thus, variations are not to be regarded as a departure from the spirit and scope of the present teachings.

What is claimed is:

1. A driver for a medical fastener, said driver comprising:
    a shaft having a generally hollow center portion configured to retain a portion of a fastener therein after the portion is separated from a fastening portion of the fastener;
    a retainer assembly coupled to said shaft and including a retaining member biased radially inwardly toward a center of said shaft; and
    a driving portion coupled to said shaft and extending axially outwardly from an end of said shaft, said driving portion located axially outward from said retainer assembly and including at least two axially extending protrusions configured to drivingly engage a fastener and having a stepped profile forming first and second portions of said protrusions, said first portion disposed axially outwardly relative to said second portion and having an outer diameter generally less than an outer diameter of said second portion.

2. The driver of claim 1, wherein said shaft includes an inner wall defining said generally hollow center, said inner wall including an alignment feature thereon.

3. The driver of claim 2, wherein said alignment feature is disposed radially inwardly relative to another portion of said inner wall.

4. The driver of claim 1, wherein said driving portion forms an end of said shaft.

5. The driver of claim 4, wherein said retainer assembly is disposed axially inwardly relative to said driving portion.

6. The driver of claim 1, wherein said retainer assembly is configured to prevent a separated portion of a fastener from exiting said shaft.

7. The driver of claim 1, wherein said driver includes an alignment feature on an outer surface thereof configure to provide an aligned orientation between a fastener cartridge and said driver.

8. In a medical driver assembly including a fastener and a driver, the fastener including a head having a driving feature extending into a first surface thereof, a shank extending from a second surface of the head opposite the first surface, and a breakaway portion extending from the first surface and configured to be selectively detached from the first surface and including a first end portion and a retention portion having a diameter less than a diameter of the first end portion and disposed axially between the first end portion and the head, the driver including a shaft, a driving portion, and a retainer assembly, the shaft including a generally hollow center portion configured to contain the breakaway portion of the fastener once it has been detached from the first portion of the head, the driving portion coupled to the shaft, located axially outward from the retainer assembly and drivingly engaged with the first driving feature of the fastener, the retainer assembly being coupled to the shaft and including a retaining member biased radially inwardly and engaging the retention portion to retain the fastener to the driver.

9. The medical driver assembly of claim 8, wherein the breakaway portion of the fastener includes a second end portion disposed between the retention portion and the head and having a diameter greater than the diameter of the retention portion, the retaining member extending into the retention portion.

10. The medical driver assembly of claim 8, wherein the driving feature includes first and second recesses formed in the first surface of the fastener head and disposed in an outer circumferential portion thereof, the driving portion of the driver extending axially outwardly from an end of the shaft and including at least two axially extending protrusions engaged with the first and second recesses.

11. The medical driver assembly of claim 8, wherein the first surface forms a first axial end of the head and the second surface forms a second axial end of the head.

* * * * *

UNITED STATES PATENT AND TRADEMARK OFFICE
CERTIFICATE OF CORRECTION

| | | |
|---|---|---|
| PATENT NO. | : 7,846,167 B2 | |
| APPLICATION NO. | : 11/593447 | |
| DATED | : December 7, 2010 | |
| INVENTOR(S) | : Saddy R. Garcia et al. | |

It is certified that error appears in the above-identified patent and that said Letters Patent is hereby corrected as shown below:

Column 7, line 23, "121" should be --12I--.
Column 7, line 25, "311" should be --31I--.
Column 7, line 25, "121" should be --12I--.
Column 8, line 54, "121" should be --12I--.
Column 13, line 29, "121" should be --12I--.
Column 14, line 65, "form a" should be --form of a--.
Column 16, line 62, Claim 7, "configure" should be --configured--.

Signed and Sealed this
Nineteenth Day of April, 2011

David J. Kappos
*Director of the United States Patent and Trademark Office*